US012788920B2

(12) United States Patent
Holley

(10) Patent No.: US 12,788,920 B2
(45) Date of Patent: Nov. 10, 2026

(54) PATIENT INTERFACES AND COMPONENTS THEREOF

(71) Applicant: RESMED PTY LTD, Bella Vista (AU)

(72) Inventor: Liam Holley, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 773 days.

(21) Appl. No.: 18/113,587

(22) Filed: Feb. 23, 2023

(65) Prior Publication Data

US 2023/0263982 A1 Aug. 24, 2023

(30) Foreign Application Priority Data

Feb. 23, 2022 (AU) ................................ 2022900411

(51) Int. Cl.
*A61M 16/06* (2006.01)
*A61M 16/00* (2006.01)

(52) U.S. Cl.
CPC .... *A61M 16/0616* (2014.02); *A61M 16/0003* (2014.02); *A61M 16/0075* (2013.01); *A61M 16/0694* (2014.02)

(58) Field of Classification Search
CPC ......... A61M 16/06–0694; A61M 16/08–0891; A61M 16/0003; A61M 16/0075
See application file for complete search history.

(56) References Cited

U.S. PATENT DOCUMENTS 4,782,832 A 11/1988 Trimble et al.
4,944,310 A 7/1990 Sullivan
5,355,878 A 10/1994 Griffiths et al.
5,687,715 A 11/1997 Landis
6,532,959 B1 3/2003 Berthon-Jones
6,581,594 B1 6/2003 Drew et al.
7,866,944 B2 1/2011 Kenyon et al.
8,636,479 B2 1/2014 Kenyon et al.
8,638,014 B2 1/2014 Sears et al.
8,733,349 B2 5/2014 Bath et al.
10,300,235 B2 5/2019 Romagnoli et al.
2008/0060649 A1* 3/2008 Veliss ............... A61M 16/0616 128/207.18
2009/0044808 A1 2/2009 Guney et al.
2009/0050156 A1 2/2009 Ng et al.
(Continued)

FOREIGN PATENT DOCUMENTS

WO WO 98/04310 A1 2/1998
WO WO 98/034665 A1 8/1998
(Continued)

OTHER PUBLICATIONS

"*Respiratory Physiology*", by John B. West, Lippincott Williams & Wilkins, 9th edition published 2012 (8 pages).

*Primary Examiner* — Valerie L Woodward
(74) *Attorney, Agent, or Firm* — Nixon & Vanderhye P.C.

(57) ABSTRACT

A patient interface includes a plenum chamber, a seal-forming structure to form a seal with or around the patient's nose and/or mouth, a positioning and stabilising structure to hold the seal-forming structure in a sealing position, and at least one inflatable body. The patient interface may limit or prevent mouth leak or mandible movement during CPAP therapy, adjust the fit of the positioning and stabilising structure on the patient's head, and/or improve the seal formed with patient's face in use.

18 Claims, 32 Drawing Sheets

(56) References Cited

U.S. PATENT DOCUMENTS

| | | | |
|---|---|---|---|
| 2010/0000534 A1 | 1/2010 | Kooij et al. | |
| 2010/0000543 A1* | 1/2010 | Berthon-Jones | A61M 16/0605 128/206.26 |
| 2010/0319700 A1 | 12/2010 | Ng et al. | |
| 2012/0080035 A1 | 4/2012 | Guney et al. | |
| 2016/0089261 A1* | 3/2016 | Quinn | A61M 16/06 128/848 |
| 2017/0326320 A1 | 11/2017 | Baigent et al. | |
| 2018/0008452 A1* | 1/2018 | Wade | A61F 5/56 |
| 2019/0022343 A1* | 1/2019 | Kooij | A61M 16/06 |
| 2019/0298958 A1 | 10/2019 | O'Connor | |
| 2023/0218427 A1* | 7/2023 | Kahlert | A61M 16/0003 128/848 |
| 2024/0058559 A1* | 2/2024 | Rafiqpoor | A61M 16/0409 |

FOREIGN PATENT DOCUMENTS

| | | |
|---|---|---|
| WO | WO 2000/078381 A1 | 12/2000 |
| WO | WO 2004/071565 | 8/2004 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/140514 | 10/2012 |
| WO | WO 2012/171072 A1 | 12/2012 |
| WO | WO 2013/020167 | 2/2013 |
| WO | WO 2015/020535 | 2/2015 |
| WO | WO 2020/191463 | 10/2020 |
| WO | WO 2021/102518 | 6/2021 |

* cited by examiner

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Relatively Large
Positive Curvature

Relatively Small
Positive Curvature

Zero Curvature

Relatively Small
Negative Curvature

Relatively Large
Negative Curvature

Copyright 2015 ResMed Limited

Copyright 2015 ResMed Limited

Copyright 2015 ResMed Limited

Copyright 2015 ResMed Limited

PATIENT INTERFACES AND COMPONENTS THEREOF

CROSS-REFERENCE TO RELATED APPLICATION(S)

This application claims priority to Australian Provisional Application No. 2022900411 filed Feb. 23, 2022, the entire contents of which are hereby incorporated by reference.

1 BACKGROUND OF THE TECHNOLOGY

1.1 Field of the Technology

The present technology relates to one or more of the screening, diagnosis, monitoring, treatment, prevention and amelioration of respiratory-related disorders. The present technology also relates to medical devices or apparatus, their use, and methods of manufacturing the devices and apparatus or components therefor.

1.2 Description of the Related Art

1.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient CO2 to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

1.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

1.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

1.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, noisy or difficult to use a patient may not comply with therapy.

Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFTTM nasal pillows mask, SWIFTTM II nasal pillows mask, SWIFTTM LT nasal pillows mask, SWIFTTM FX nasal pillows mask and MIRAGE LIBERTYTM full-face mask. The following patent applications, assigned to ResMed Limited, describe examples of nasal pillows masks: International Patent Application WO2004/073,778 (describing amongst other things aspects of the ResMed Limited SWIFTTM nasal pillows), US Patent Application 2009/0044808 (describing amongst other things aspects of the ResMed Limited SWIFTTM LT nasal pillows); International Patent Applications WO 2005/063,328 and WO 2006/130,903 (describing amongst other things aspects of the ResMed Limited MIRAGE LIBERTYTM full-face mask); International Patent Application WO 2009/052,560 (describing amongst other things aspects of the ResMed Limited SWIFTTM FX nasal pillows).

The use of a patient interface which is in the form of a nasal mask, e.g. nasal CPAP therapy, may cause mouth leak or mandible movement. The patient may inadvertently open their mouth or otherwise compromise the lip seal when the pressure of the gas or the flow of gas in the nasal mask is increased.

A person's lips may be capable of sealing against a moderate level of oral pressure with conscious control of the various muscles involved, such as, for example, for a brief period at the beginning of articulating a 'p' or 'b' sound, or the lips may consciously seal against negative pressure, such as when a person is underwater. Similarly, most people are able to consciously maintain a lip seal during positive airway pressure therapy administered via a nasal interface. However, during sleep, and particularly during rapid eye movement (REM) sleep, there is commonly a reduction in muscle tone and a loss of control of the muscles and the intentional acting to hold the mandible in place and seal the lips, and as such many people undergoing nasal positive airway pressure therapy during sleep may develop mouth leak. This may lead to side-effects such as dryness in the mouth and throat.

One known method of avoiding mouth leak or mandible movement is the use of a chin strap. This may take the form of a sling for the patient's chin attached to a strap which loops from one side of the sling, over the top of the patient's head to the opposite side of the sling.

Such a sling may be a simple and effective means of preventing mandible depression. However, one disadvantage may be that the strap must be tensioned tightly enough to prevent mandible movement at the highest potential therapy pressure the patient will be exposed to. This may mean that the tension is greater than is necessary to resist mandible movement at other times, for example if the RPT device is providing lower pressure while the patient falls asleep. This excess strap tension may make it more difficult for the patient to fall asleep, and may increase the chances of marking the patient's skin.

1.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

1.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

1.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

1.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2: 2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed MirageTM (*) | nasal | 29.5 | 21.5 | 1998 |
| ResMed UltraMirageTM | nasal | 36 (3) | 28 (3) | 2000 |
| ResMed Mirage ActivaTM | nasal | 32 (3) | 24 (3) | 2002 |
| ResMed Mirage MicroTM | nasal | 30 (3) | 22 (3) | 2008 |
| ResMed MirageTM SoftGel | nasal | 29 (3) | 22 (3) | 2008 |
| ResMed MirageTM FX | nasal | 26 (3) | 18 (3) | 2010 |
| ResMed Mirage SwiftTM (*) | nasal pillows | 37 | 29 | 2004 |
| ResMed Mirage SwiftTM II | nasal pillows | 28 (3) | 20 (3) | 2005 |

-continued

Table of noise of prior masks (ISO 17510-2: 2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| ResMed Mirage SwiftTM LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

According to an aspect of the technology a hoop structure for reducing or eliminating mouth drop in a patient during respiratory pressure therapy is provided, the hoop structure comprising:

a top portion configured to extend over a top of the patient's head;

a chin portion configured to extend below the patient's chin or lower jaw; and an inflatable body positioned, in use, between a portion of the hoop structure and the patient's head.

According to an aspect of the present technology there is provided a patient interface comprising a plenum chamber pressurisable to a therapeutic pressure of at least 4 cmH2O above ambient air pressure, the plenum chamber including:

at least one plenum chamber inlet port sized and structured to receive a flow of air at the therapeutic pressure for breathing by a patient;

a seal-forming structure that is constructed and arranged to form a seal with a region of the patient's face surrounding an entrance to the patient's airways, the seal-forming structure having a hole therein such that the flow of air at said therapeutic pressure is delivered to at least an entrance to the patient's nares, wherein the seal-forming structure is constructed and arranged to maintain said therapeutic pressure in the plenum chamber throughout the patient's respiratory cycle in use, the patient interface further comprising a positioning and stabilising structure to provide a force to hold the seal-forming structure in a therapeutically effective position on the patient's head, the patient interface further comprising a hoop structure comprising:

a top portion configured to extend over a top of the patient's head;

a chin portion configured to extend below the patient's chin or lower jaw; and an inflatable body positioned, in use, between a portion of the hoop structure and the patient's head.

According to an aspect of the technology a patient interface comprises a plenum chamber pressurisable to a therapeutic pressure of at least 4 cmH2O above ambient air pressure, the plenum chamber including:

at least one plenum chamber inlet port sized and structured to receive a flow of air at the therapeutic pressure for breathing by a patient;

a seal-forming structure that is constructed and arranged to form a seal with a region of the patient's face surrounding an entrance to the patient's airways, the seal-forming structure having a hole therein such that the flow of air at said therapeutic pressure is delivered to at least an entrance to the patient's nares, wherein the seal-forming structure is constructed and arranged to maintain said therapeutic pressure in the plenum chamber throughout the patient's respiratory cycle in use, the patient interface further comprising a positioning and stabilising structure to provide a force to hold the seal-forming structure in a therapeutically effective position on the patient's head, the patient interface further comprising a chin portion configured to extend below the patient's chin or lower jaw, the chin portion connected to the positioning and stabilising structure, the plenum chamber, or a frame of the patient interface, and an inflatable body positioned, in use, between the chin portion and the patient's chin or lower jaw.

According to an aspect of the present technology there is provided a patient interface, wherein the patient interface comprises:

a plenum chamber configured to receive in use a flow of air at the therapeutic pressure for breathing by a patient, a seal-forming structure configured to form a seal in use with or around portions of the patient's nose, and a positioning and stabilising structure configured to hold the seal-forming structure in a sealing position, wherein at least one inflatable body is provided to the positioning and stabilising structure, and wherein the at least one inflatable body is configured to limit or prevent mouth leak or mandible movement during CPAP therapy.

According to an aspect of the present technology there is provided a patient interface, wherein the patient interface comprises:

a plenum chamber configured to receive in use a flow of air at the therapeutic pressure for breathing by a patient, a seal-forming structure configured to form a seal in use with or around portions of the patient's nose, and a positioning and stabilising structure configured to hold the seal-forming structure in a sealing position, wherein at least one inflatable body is provided to the positioning and stabilising structure, and wherein the at least one inflatable body is configured to adjust the fit of the positioning and stabilising structure on the patient's head.

According to an aspect of the present technology there is provided a patient interface, wherein the patient interface comprises:

a plenum chamber configured to receive in use a flow of air at the therapeutic pressure for breathing by a patient, a seal-forming structure configured to form a seal in use with or around portions of the patient's nose, and a positioning and stabilising structure configured to hold the seal-forming structure in a sealing position, wherein at least one inflatable body is provided to the positioning and stabilising structure, and wherein the positioning and stabilising structure comprises a chin portion which extends in use below the patient's chin and/or lower jaw region, and wherein the at least one inflatable body is configured to limit or prevent mouth leak or mandible movement during CPAP therapy, and/or adjust the fit of the positioning and stabilising structure on the patient's head.

According to an aspect of the present technology there is provided a patient interface, wherein the patient interface comprises:

a plenum chamber configured to receive in use a flow of air at the therapeutic pressure for breathing by a patient, a seal-forming structure configured to form a seal in use with or around portions of the patient's nose, a chin portion which extends in use below the patient's chin and/or lower jaw region, a top portion which extends in use over the top of the patient's head, and an inflatable body, wherein the chin portion and the top portion are connected to each other to form a hoop structure which loops in use around the patient's head, and wherein the inflatable body is positioned in use between a region of the patient's head and a portion of the hoop structure.

According to an aspect of the present technology there is provided a patient interface, wherein the patient interface comprises:

a plenum chamber configured to receive in use a flow of air at the therapeutic pressure for breathing by a patient, a seal-forming structure configured to form a seal in use with or around portions of the patient's nose, at least one strap configured to hold the seal-forming structure in a sealing position, a chin strap which extends in use below the patient's chin and/or lower jaw region, and an inflatable body, wherein the chin strap connects to at least one of the strap(s), the plenum chamber and the seal-forming structure, and wherein the inflatable body is positioned in use between a region of the patient's head and at least one of the chin portion and the strap(s).

According to an aspect of the present technology there is provided a hoop structure configured to limit or prevent mouth leak or mandible movement during CPAP therapy, wherein the hoop structure comprises:

a chin portion which extends in use below the patient's chin and/or lower jaw region, a top portion which extends in use over the top of the patient's head, and an inflatable body, wherein the chin portion and the top portion are connected to each other such that the hoop structure loops in use around the patient's head, and wherein the inflatable body is positioned in use between a region of the patient's head and a portion of the hoop structure.

According to an aspect of the present technology there is provided a positioning and stabilising structure configured to hold a seal-forming structure of a patient interface in a sealing position on a patient's face, wherein the positioning and stabilising structure comprises:

a chin strap which extends in use below the patient's chin and/or lower jaw region, a top strap which extends in use over the top of the patient's head, and an inflatable body, wherein the chin strap and the top strap are connected to each other to form a hoop structure which loops in use around the patient's head, and wherein the inflatable body is positioned in use between a region of the patient's head and a portion of the hoop structure.

In an example, the patient interface may be in the form of a nasal mask.

In an example, the inflatable body may be inflated by a fluid from a deflated condition to an inflated condition. For instance, the inflatable body may be inflated by a pressurised gas which is breathable.

In an example, the inflatable body may be configured to expand and compress. For instance, the inflatable body may be substantially hollow and may be formed from a soft, flexible material.

In an example, the inflatable body may be configured to facilitate expansion and compression of the inflatable body. For instance, the inflatable body may comprise one or more folds and/or thinned regions.

In an example, the patient interface may further comprise a connection port which is configured to receive a supply of pressurised breathable gas.

In an example, the inflatable body may be configured to receive in use a pressurised gas. For instance, the inflatable body may comprise an inlet configured to receive the supply of fluid, e.g. the supply of pressurised gas. The inlet may act as the connection port.

In an example, the inflatable body may be fluidly connected to the plenum chamber. For instance, the patient interface may comprise at least one conduit which fluidly connects the inflatable body to the plenum chamber. In a preferred example, the patient interface may comprise a pair of conduits.

In an example, the patient interface may comprise a top portion which extends in use over the top of the patient's head. For instance, the top portion may comprise a top strap.

In an example, the patient interface may comprise a chin portion which extends in use below the patient's chin and/or lower jaw region. For instance, the chin portion may comprise a chin strap.

In an example, the chin portion and the top portion may be connected to each other to form a hoop structure which loops around the patient's head. For instance, the inflatable body may be provided to a portion of the hoop structure.

In an example, the chin portion may be integrally formed with the top portion. For instance, the chin strap may be integrally formed with the top strap.

In an example, the patient interface may comprise a positioning and stabilising structure. For instance, the positioning and stabilising structure may comprise one or more straps.

In an example, the chin portion may be connected to the positioning and stabilising structure.

In an example, the positioning and stabilising structure may comprise the chin portion. For instance, the chin strap may form part of the positioning and stabilising structure.

In an example, the top portion may be connected to the positioning and stabilising structure.

In an example, the positioning and stabilising structure may comprise the top portion. For instance, the top strap may form part of the positioning and stabilising structure.

In an example, the positioning and stabilising structure may comprise a rear portion which extends in use around the rear of the patient's head. For instance, the positioning and stabilising structure may comprise a rear strap.

In an example, the chin strap may be connected to at least one of the rear strap and the top strap.

In an example, the chin strap may be connected to at least one of the plenum chamber, the seal-forming structure, and a component attached to or formed with the plenum chamber and/or the seal-forming structure.

In an example, an inflatable body may be located in use proximate at least one region of the patient's head and/or face. For instance, the inflatable body may engage in use with a region of the patient's face and/or head when the inflatable body is inflated.

In an example, the inflatable body may be positioned in use between the patient's head and/or face, and at least one of the chin portion and the top portion.

In an example, the inflatable body may be located in use below the patient's chin and/or lower jaw region. For instance, the inflatable body may engage in use with the patient's chin and/or lower jaw region when the inflatable body is inflated.

In an example, the inflatable body may be positioned in use between the patient's chin and/or lower jaw region and the chin portion. For instance, the inflatable body may be positioned in use between the patient's chin and/or lower jaw region and the chin strap.

In an example, the inflatable body may be located in use on top of the patient's head. For instance, the inflatable body may engage in use with the top of the patient's head when the inflatable body is inflated.

In an example, the inflatable body may be positioned in use between the top of the patient's head and the top portion. For instance, the inflatable body may be positioned in use between the top of the patient's head and the top strap.

In an example, the chin portion may connect to the inflatable body at a connection point. For instance, the chin strap may connect to the inflatable body at the connection point.

In an example, the top portion may connect to the inflatable body at a connection point. For instance, the top strap may connect to the inflatable body at the connection point.

In an example, the connection point may be located in a region of the inflatable body which permits the inflatable body to be inflated and expand in use in a direction extending away from the connection point and towards the patient's head. For instance, the connection point may be located on an inferior region of the inflatable body connected to the chin portion, and/or the connection point may be located on a superior region of the inflatable body connected to the top portion.

In an example, the positioning and stabilising structure may be structured and arranged to be tensioned or tightened on the patient's head. For instance, the inflatable body may be configured to tension or tighten the positioning and stabilising structure on the patient's head.

In an example, a first region of the inflatable body may contact in use a region of the patient's head. For instance, the first region may be a superior region of the inflatable body which contacts in use a region of the patient's head under the patient's chin and/or lower jaw region, and/or the first region may be an inferior region of the inflatable body which contacts in use a region of the top of the patient's head.

In an example, the connection point may be located further away from the patient's head when the inflatable body is in an/the inflated condition.

In an example, the chin portion may be tensioned or tightened when the connection point is located further away from the patient's head. For instance, the chin strap may be tensioned or tightened when the connection point is located further away from the patient's head.

In an example, the patient interface may be configured to limit or prevent mouth leak or mandible movement during CPAP therapy. For instance, the inflatable body may be configured to limit or prevent mouth leak or mandible movement during CPAP therapy In an example, the inflatable body may create in use a force which acts on the patient's chin and/or lower jaw region to maintain the patient's mouth in a closed position, e.g. a chin strap force. For instance, the force may extend substantially upwards and towards the region under the patient's chin and/or lower jaw region.

In an example, the chin strap/chin portion may be tensioned or tightened to increase the force.

In an example, the patient interface may comprise one or more sensors.

In an example, the sensor(s) may be located on the inflatable body.

In an example, the sensor(s) may be configured to detect resistance to the force.

In an example, the inflatable body may be configured to adjust the fit of the positioning and stabilising structure on the patient's head.

In an example, the positioning and stabilising structure may be tensioned or tightened when the inflatable body is in an/the inflated condition.

In an example, the positioning and stabilising structure may be loosened when the inflatable body is in a/the deflated condition.

According to another aspect of the present technology there is provided a patient interface, wherein the patient interface comprises:

- a plenum chamber configured to receive, in use, a flow of air at the therapeutic pressure for breathing by a patient,
- a seal-forming structure configured to form a seal, in use, with or around portions of the patient's nose and/or mouth,
- a positioning and stabilising structure configured to hold the seal-forming structure in a sealing position, and
- a lever arrangement which is connected to the plenum chamber and/or the seal-forming structure,
- wherein an inflatable body is provided to the lever arrangement, wherein the inflatable body is positioned in use between a region of the patient's head and/or face and a portion of the lever arrangement, and wherein the inflatable body is inflated in use to create a force which acts on the lever arrangement and which is transferred to the plenum chamber and/or seal-forming structure.

In an example, the patient interface comprises a forehead support.

In an example, the forehead support may be configured to provide the lever arrangement. In an example, the lever arrangement may form part of the positioning and stabilising structure.

In an example, the plenum chamber may comprise a frame. For instance, the frame may be a substantially rigid frame.

In an example, the inflatable body may be positioned in use on a region of the patient's head and/or face. For instance, the inflatable body may be positioned in use on the patient's forehead region.

In an example, the inflatable body may be positioned in use between the lever arrangement and the region of the patient's face and/or head.

In an example, the inflatable body may be inflated in use to create a force which acts on the lever arrangement and which is transferred to the plenum chamber and/or seal-forming structure.

In an example, the patient interface may comprise a fulcrum on which the lever arrangement pivots. For instance, the lever arrangement is configured to pivot on the fulcrum when the inflatable body is inflated to create a force which acts on the plenum chamber and/or seal-forming structure and increases the sealing force of the seal-forming structure on the patient's face.

In an example, the fulcrum may be located at a connection point between a positioning and stabilising structure and the lever arrangement.

In an example, the positioning and stabilising structure includes one or more straps or portions.

In an example, the strap(s) or portion(s) may be located in use such that each strap or portion extends above the patient's eyes.

In an example, the patient interface may be provided without lower straps or portions which extend across a lower region of the patient's face.

In an example, the strap(s) or portion(s) may be connected to the lever arrangement. For instance, the strap(s) or portion(s) may be connected to the forehead support at the fulcrum. The fulcrum may be located in use proximate the patient's brow.

In an example, the patient interface may be configured to facilitate adjustment of the sealing force. For instance, the pressure inside the inflatable body may be increased or decreased to adjust the force.

In an example, the patient interface may be configured to adjust headgear tension. For instance, the patient interface decrease headgear tension when the inflatable body is deflated and increase headgear tension when the inflatable body is inflated or expanded.

In an example, the lever arrangement may comprise a conduit which is fluidly connected to the plenum chamber.

In an example, the inflatable body may be fluidly connected to the conduit.

In an example, the inflatable body may be fluidly connected to at least one of the plenum chamber, an air circuit which supplies the flow of air at the therapeutic pressure for breathing by the patient, and an RPT device.

In an example, patient interface may include a vent structure configured to allow a flow of gases exhaled by the patient from an interior of the plenum chamber to ambient.

In an example, the inflatable body may include a vent structure configured to allow a flow of gases from an interior of the inflatable body to ambient.

In an example, the inflatable body vent structure may be configured to direct the flow of vented gases therefrom onto the patient's head and/or face.

In an example, a patient contacting surface of the inflatable body may be made from at least one of a thermally conductive material and a composite material with high thermal conductivity.

In an example, the patient interface may be in the form of a nasal mask. However, the patient interface may be in the form of an oro-nasal or full-face mask.

According to another aspect of the present technology there is provided a patient interface, wherein the patient interface comprises:

a plenum chamber configured to receive in use a flow of air at the therapeutic pressure for breathing by a patient, a seal-forming structure configured to form a seal in use with or around portions of the patient's nose and/or mouth, wherein the seal-forming structure and plenum chamber define a breathing chamber, and a positioning and stabilising structure configured to hold the seal-forming structure in a sealing position, wherein the seal-forming structure comprises an inflatable body, and wherein the inflatable body is configured to limit or prevent deformation of the inflatable body in a first region and facilitate deformation in a second region.

In an example, the inflatable body may have a first wall which faces in a direction extending outwards and away from the breathing chamber and a second wall which faces in a direction extending inwards and towards the breathing chamber, wherein the first wall is stiffer than the second wall. For instance, the first wall may provide the first region, and the second wall may provide the second region.

In an example, the plenum chamber may comprise a frame. For instance, the frame may be a substantially rigid frame.

In an example, the inflatable body may extend around at least a portion of a perimeter of the seal-forming structure.

In an example, the inflatable body may engage with the patient's face in use such that it forms a seal around the patient's nose and/or mouth.

In an example, the plenum chamber may comprise a connection port which connects to an air circuit.

In an example, the inflatable body is configured to receive a supply of pressurised gas from a first conduit, and a second conduit (e.g. an air circuit) may supply the flow of air at the therapeutic pressure to the plenum chamber.

In an example, the first conduit may be fluidly connected to a bottom region of the inflatable body. For instance, the first conduit may be connected to a part of the inflatable body which is positioned below the second conduit.

In an example, the first conduit may be attached to the second conduit.

In an example, the first region may be configured to restrict deformation outwards and away from the breathing chamber, and the second region may be configured to deform inwards into the breathing chamber.

In an example, the stiffness of the inflatable body may be varied in or more regions. For instance, the inflatable body may comprise a first region and a second region, wherein the second region has a different stiffness to the first region.

In an example, the first wall may be stiffer than the second wall. For instance, the first wall may be thicker than the second wall.

In an example, the patient interface may be in the form of a full-face or oro-nasal mask.

In an example, the patient interface may be in the form of a nasal mask.

According to another aspect of the present technology there is provided a patient interface, wherein the patient interface comprises:

a plenum chamber configured to receive in use a flow of air at the therapeutic pressure for breathing by a patient, a seal-forming structure configured to form a seal in use with or around portions of the patient's nose and/or mouth, wherein the seal-forming structure and plenum chamber define a breathing chamber, and a positioning and stabilising structure configured to hold the seal-forming structure in a sealing position, wherein the seal-forming structure comprises an inflatable body and a seal flap.

In an example, the seal flap may be located more proximate to the patient's nose and/or mouth with respect to the inflatable body.

In an example, the patient interface may be configured such that the inflatable body is spaced apart from the seal flap to create a chamber therebetween.

In an example, the chamber may be defined by a plurality of walls. For instance, a first wall may be formed by a portion of the frame. A second wall may be formed by the seal flap. A third wall may formed by a wall of the inflatable body which faces in a direction extending inwards and towards the breathing chamber.

In an example, the seal-forming structure may comprise a flow path which extends from an interior of the breathing chamber, through the chamber between the seal flap and the inflatable chamber, to ambient In an example, the seal flap may comprise one or more vent holes.

In an example, the first wall, e.g. the portion of the frame, may comprise one or more vent holes.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

Figure 1A:
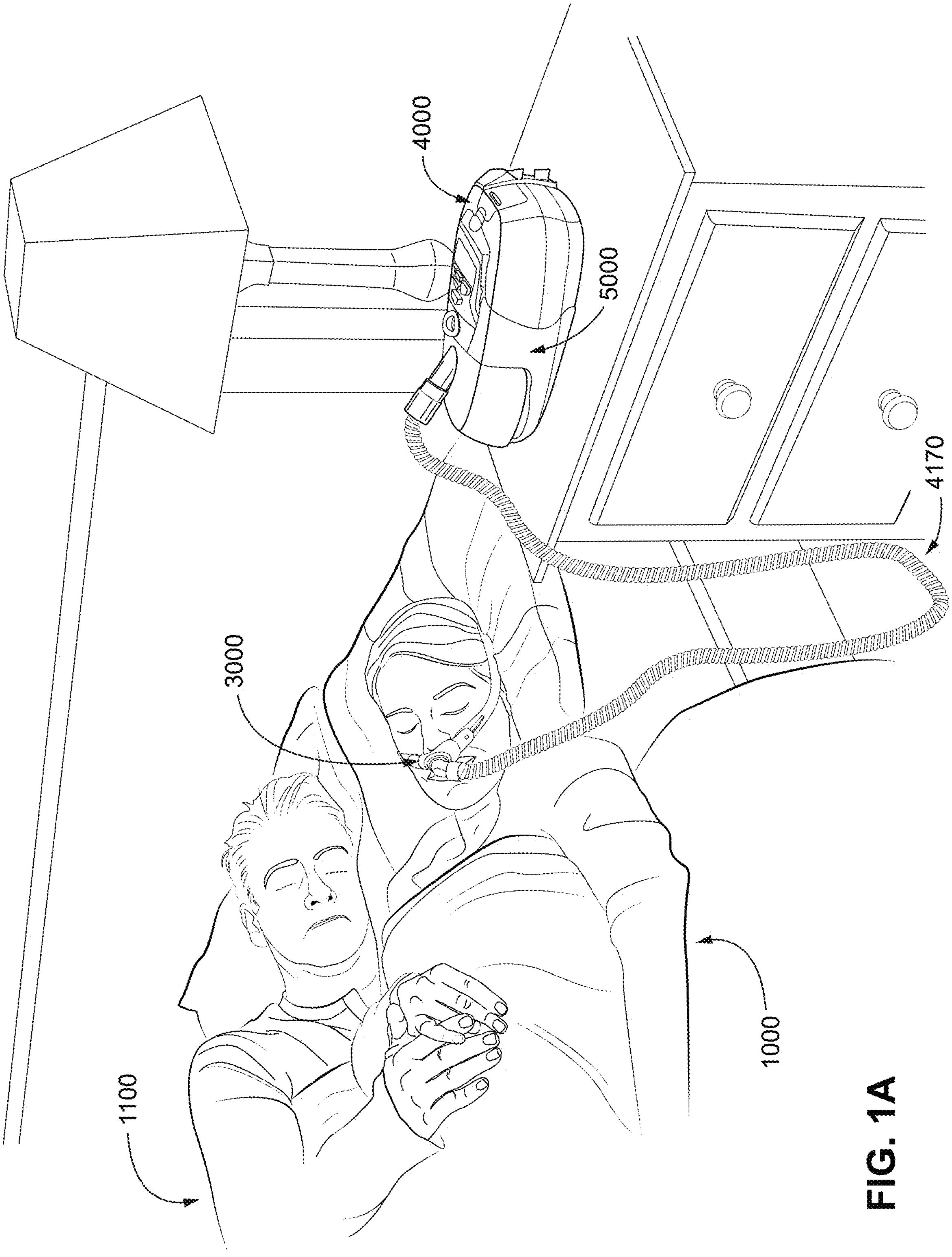
Figure 1B:
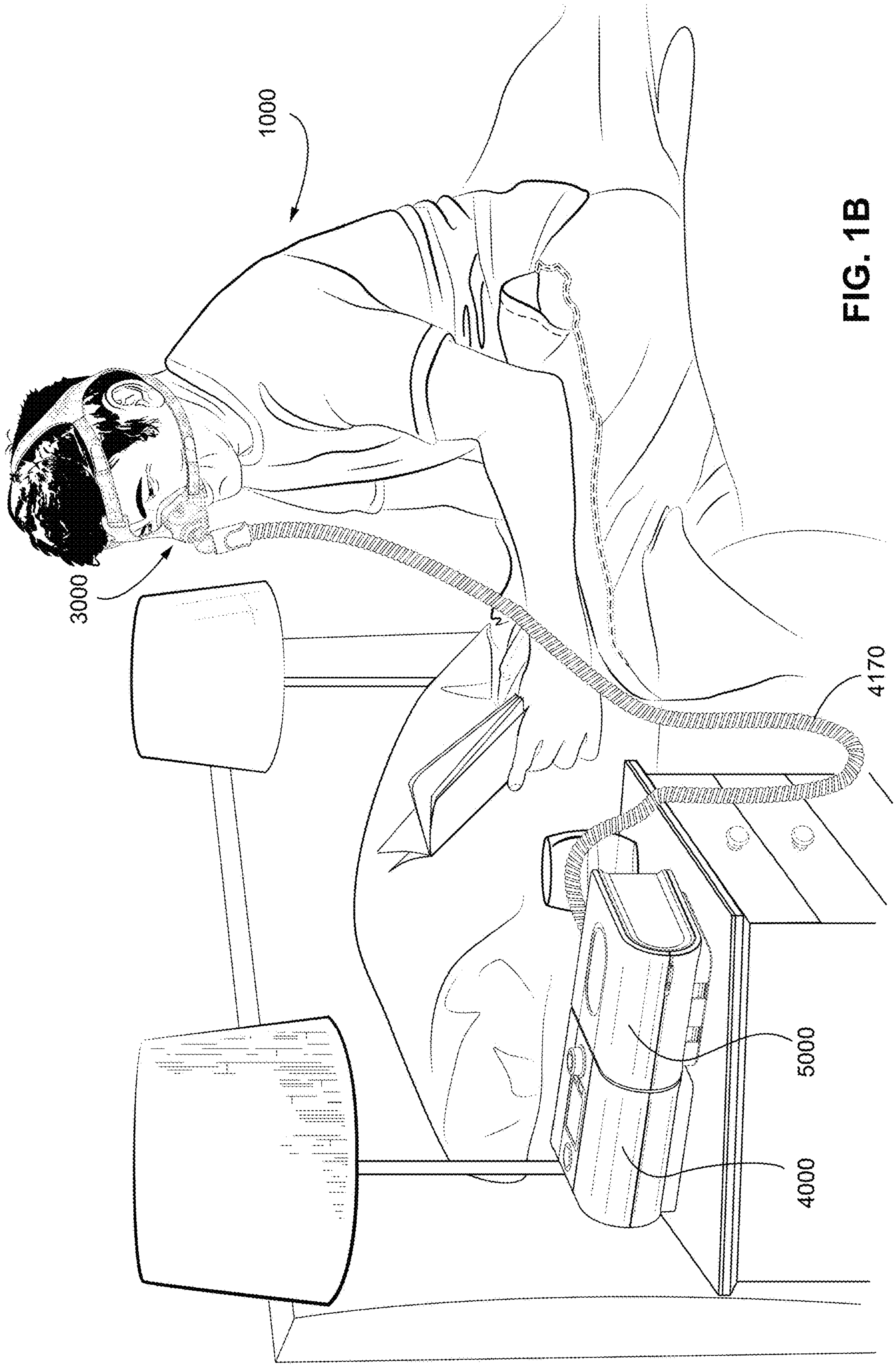
Figure 1C:
Figure 2A:
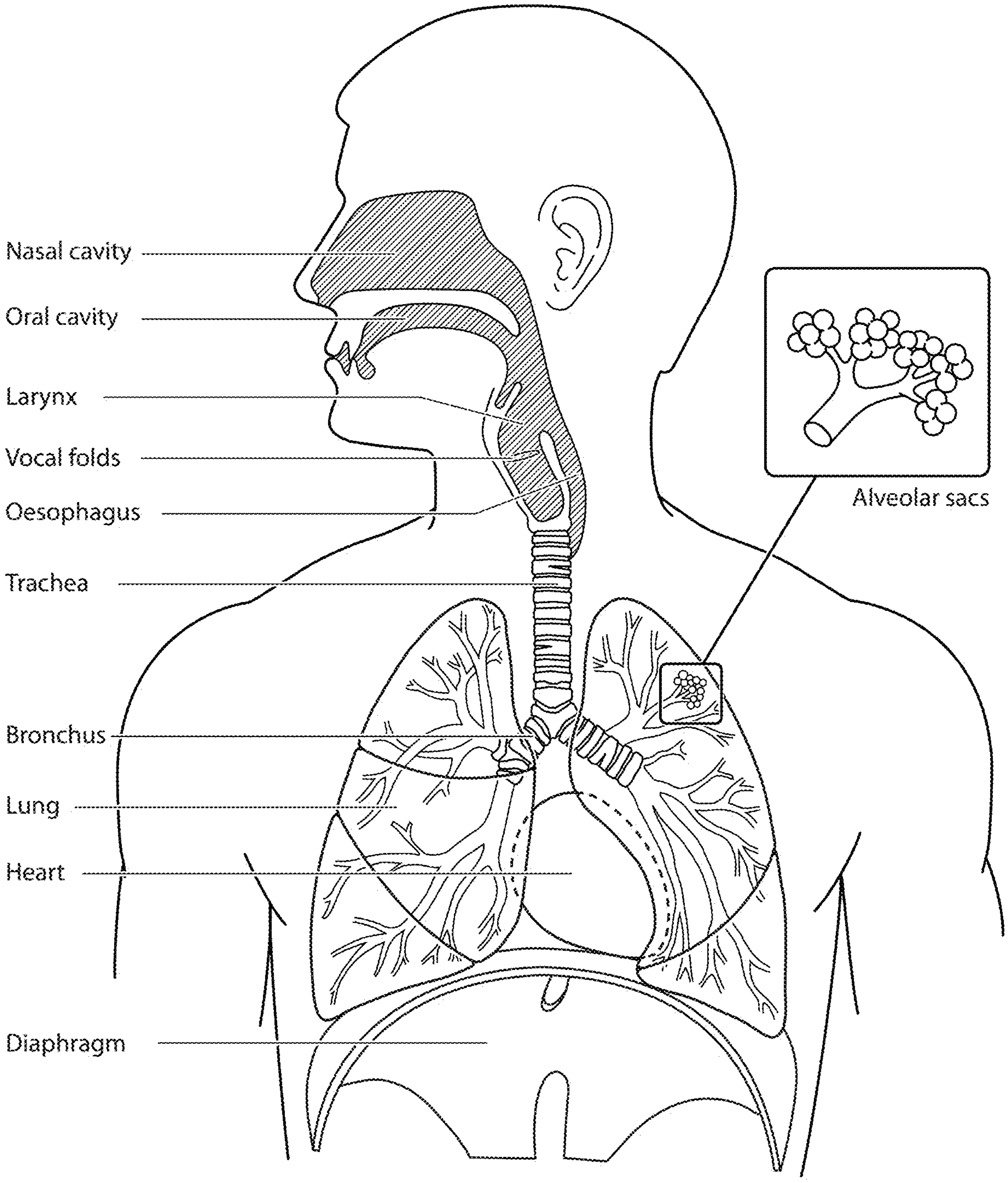
FIG. 2A shows an overview of a human respiratory system including the nasal and oral cavities, the larynx, vocal folds, oesophagus, trachea, bronchus, lung, alveolar sacs, heart and diaphragm.
Figure 2B:
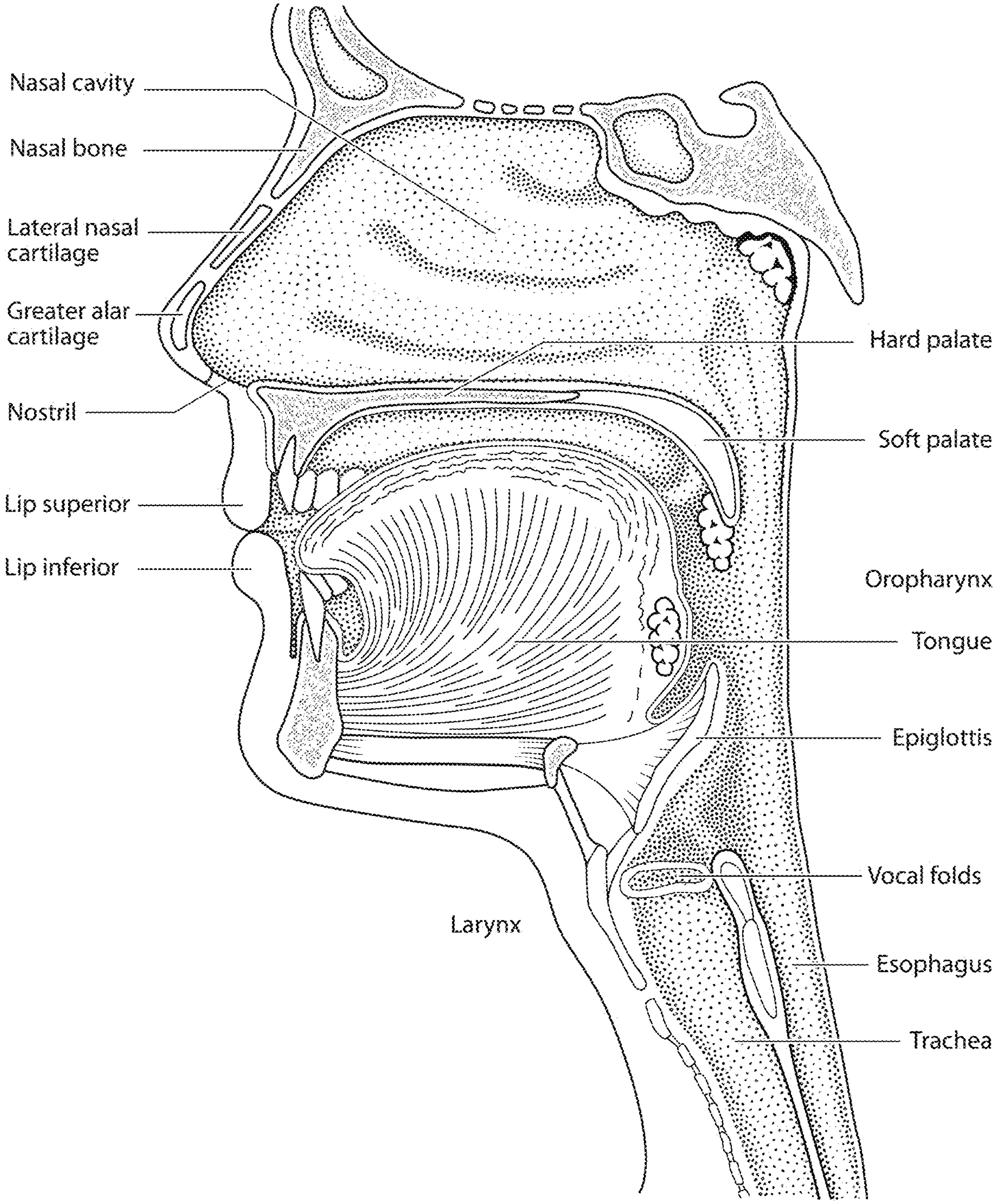
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
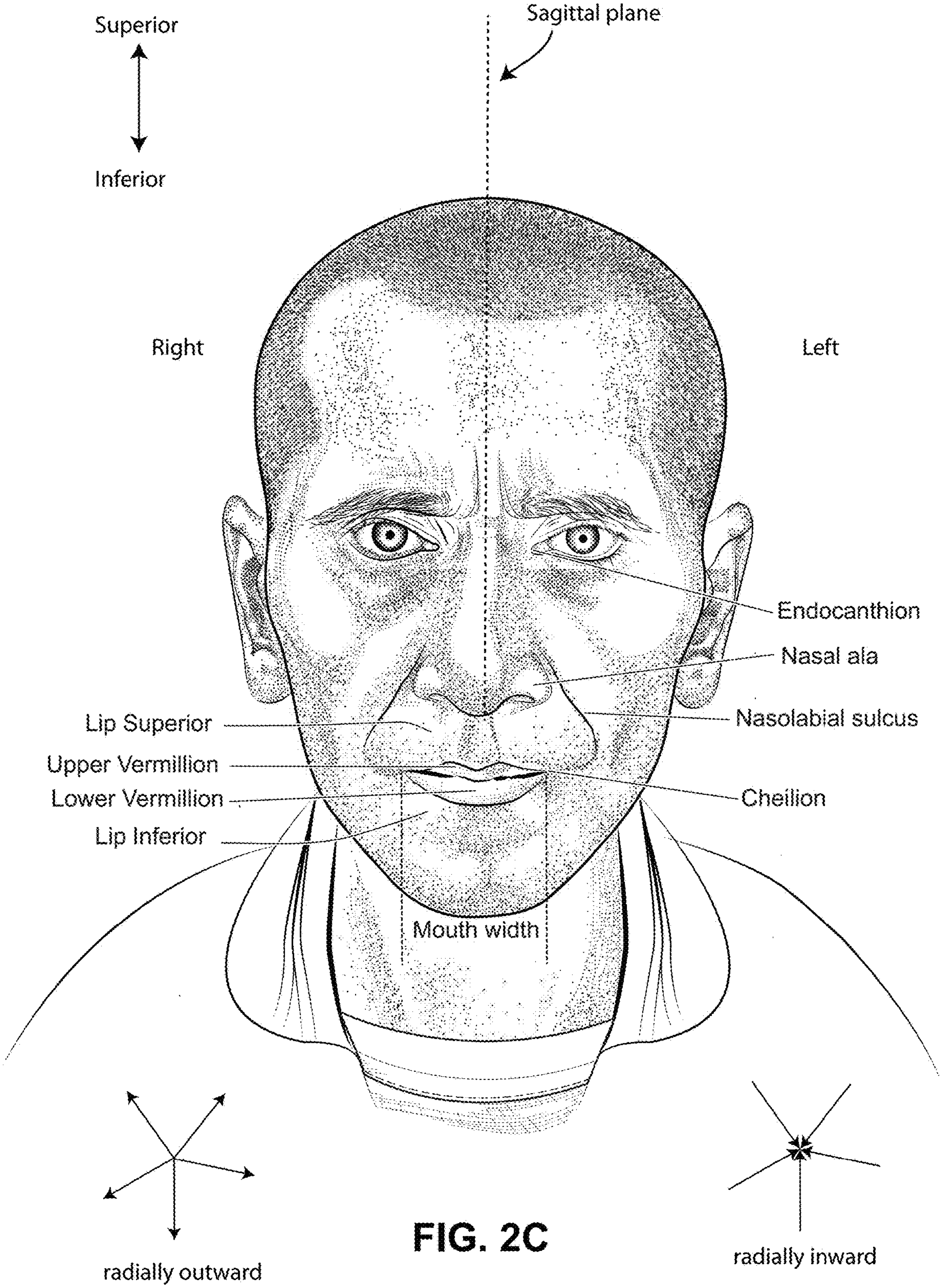
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
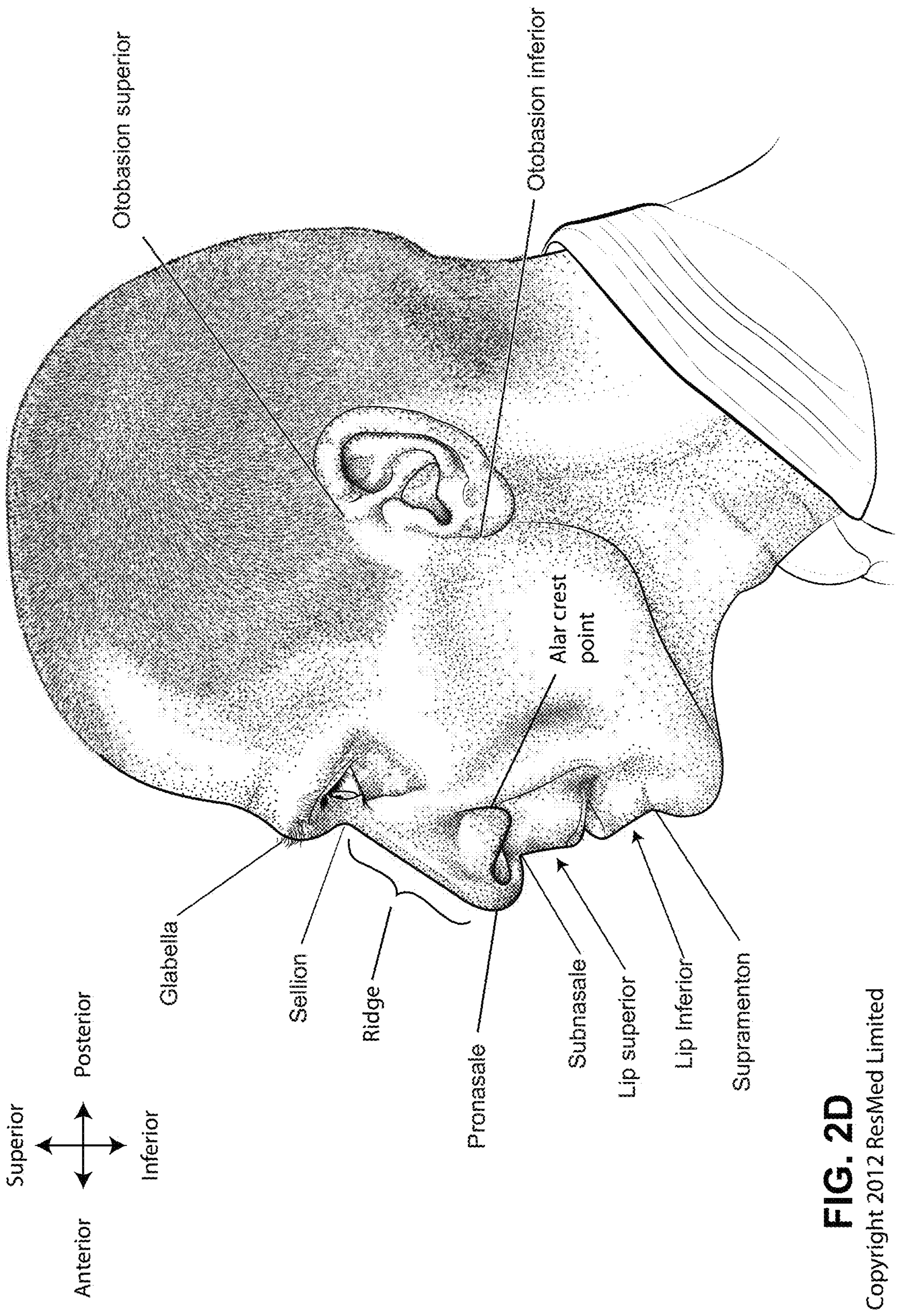
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
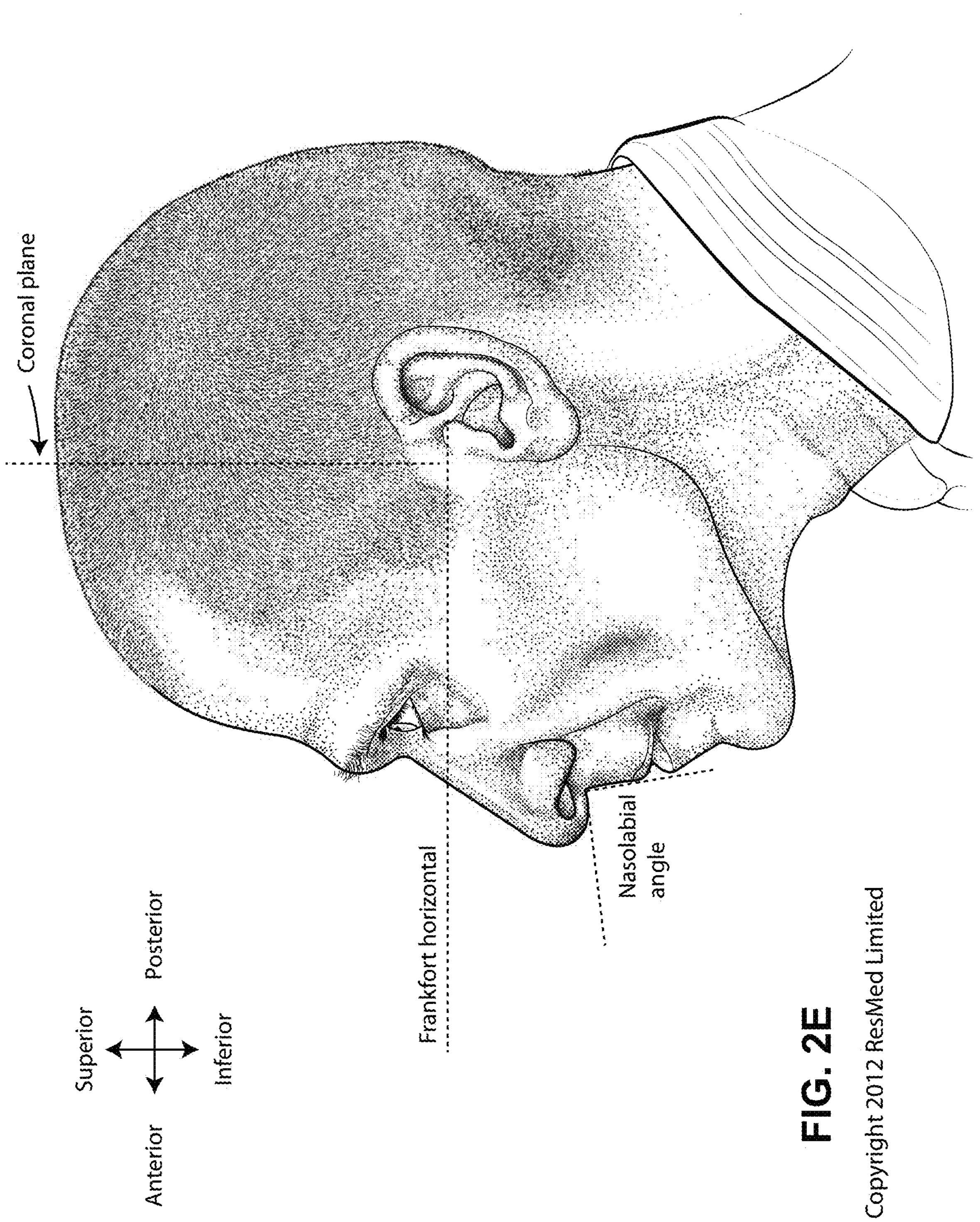

FIG. 2E is a further side view of a head. The approximate locations of the Frankfort horizontal and nasolabial angle are indicated. The coronal plane is also indicated.

Figure 2F:
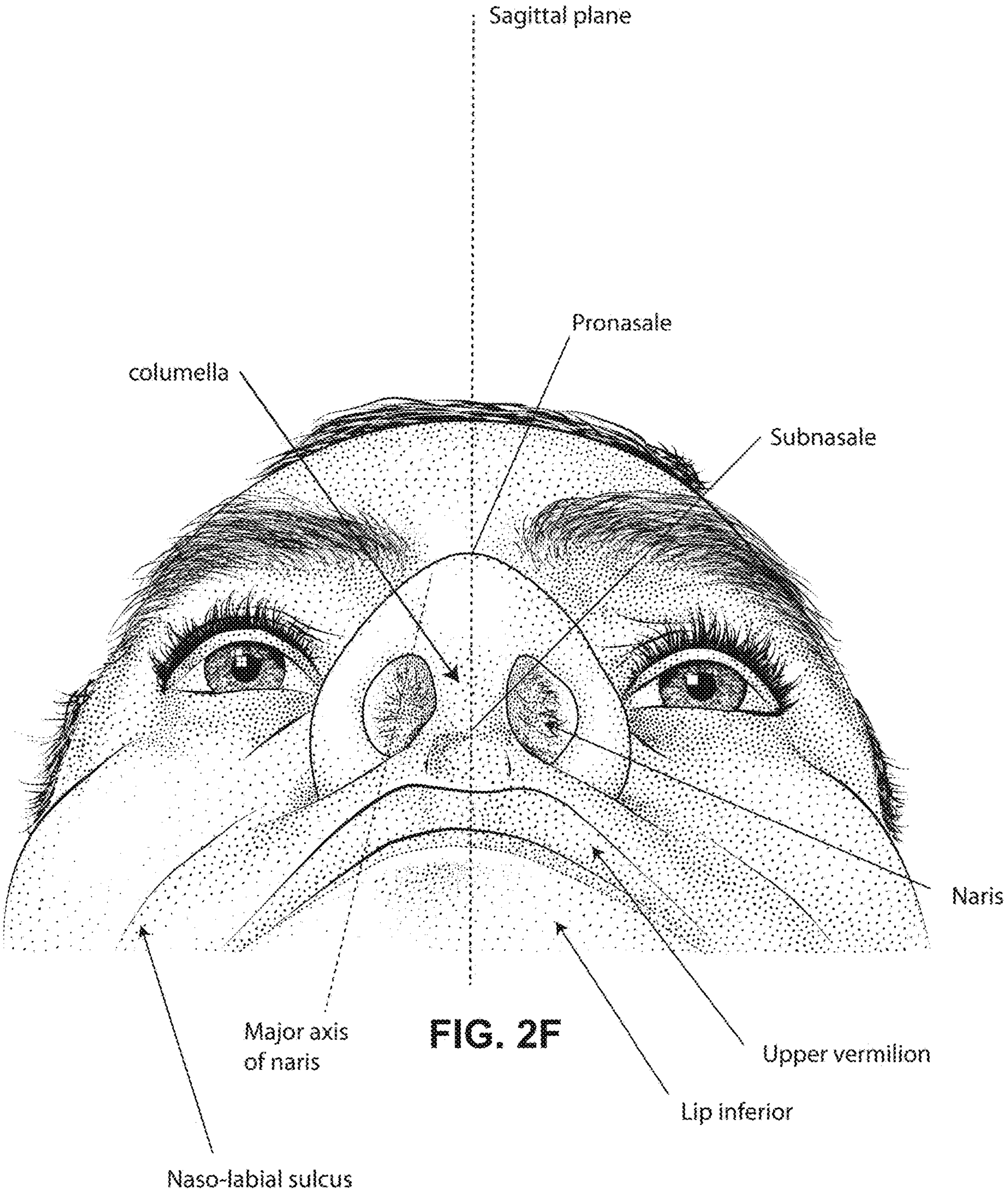

FIG. 2F shows a base view of a nose with several features identified including naso-labial sulcus, lip inferior, upper Vermilion, naris, subnasale, columella, pronasale, the major axis of a naris and the midsagittal plane.

Figure 2I:
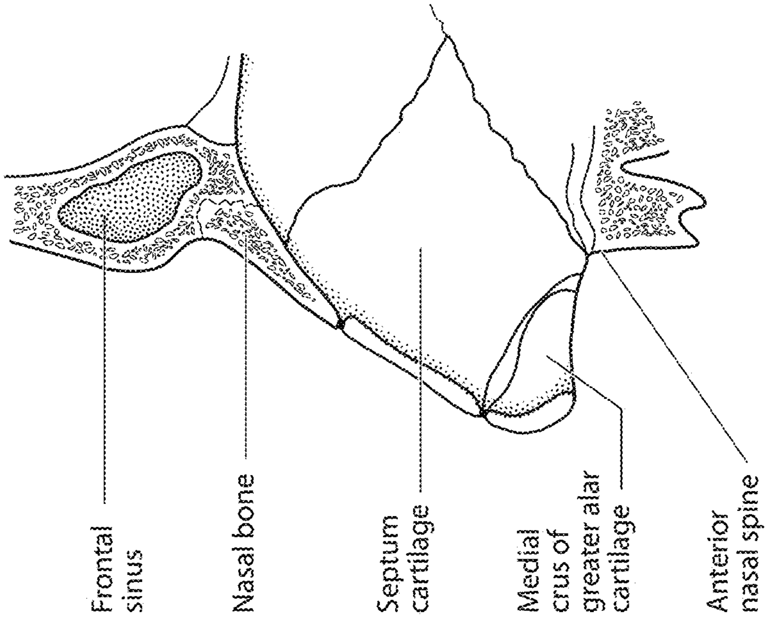
Figure 2H:
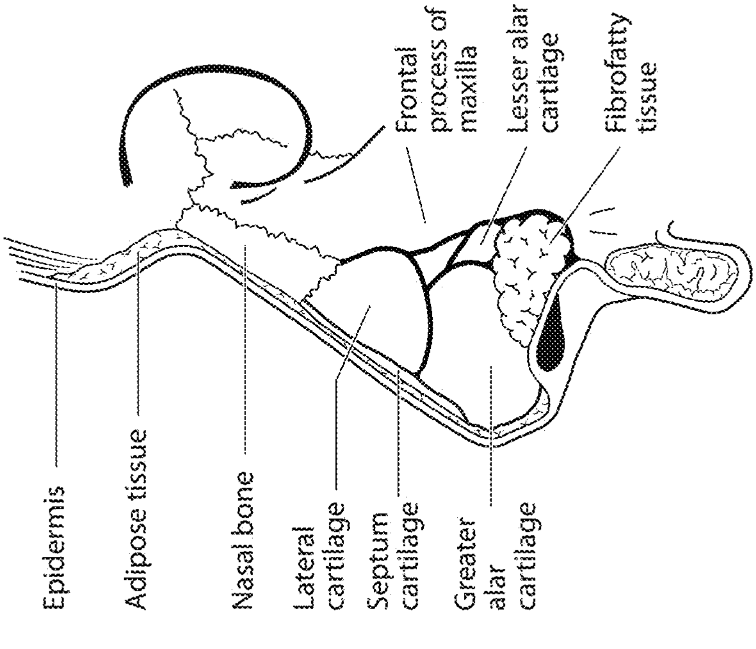
Figure 2G:

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
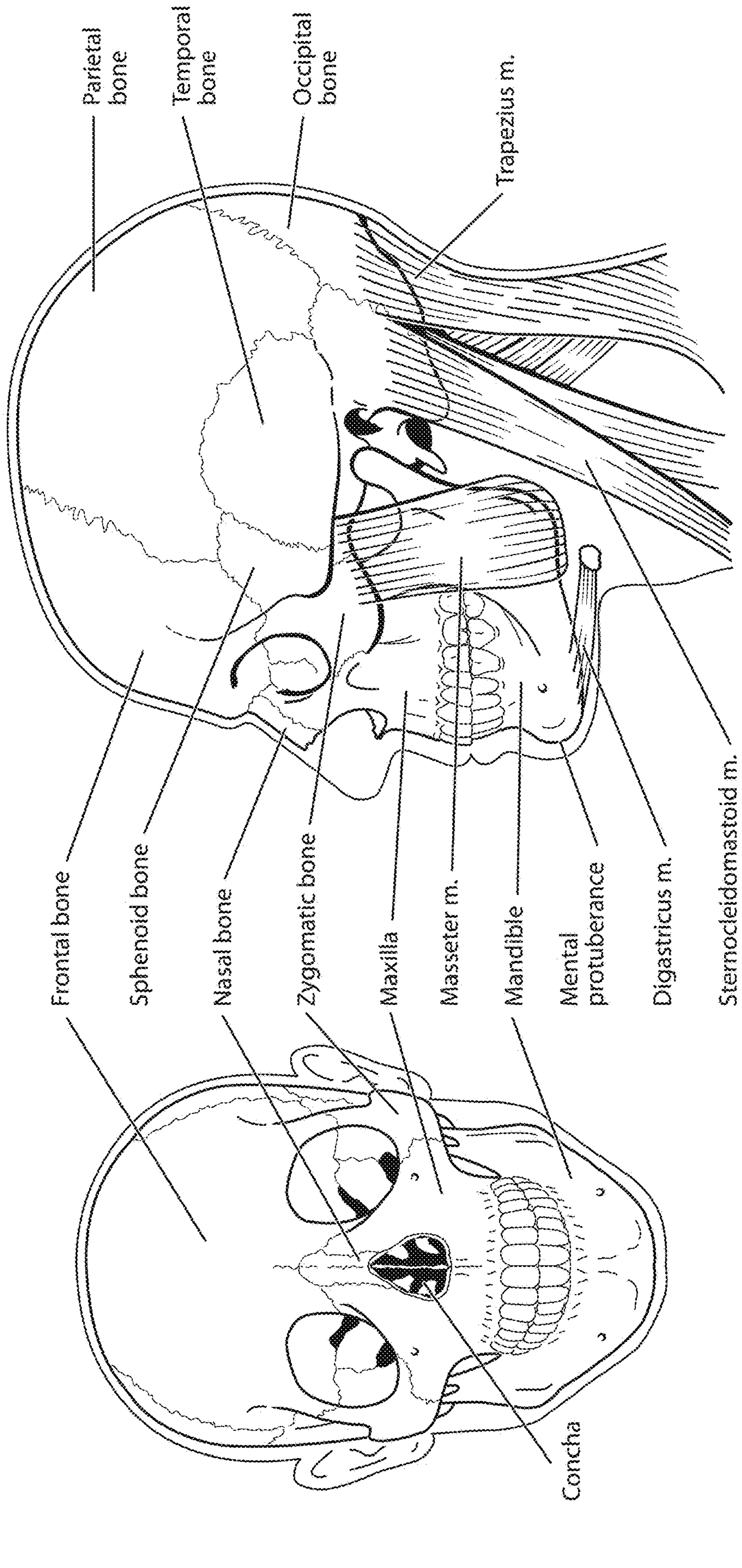

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
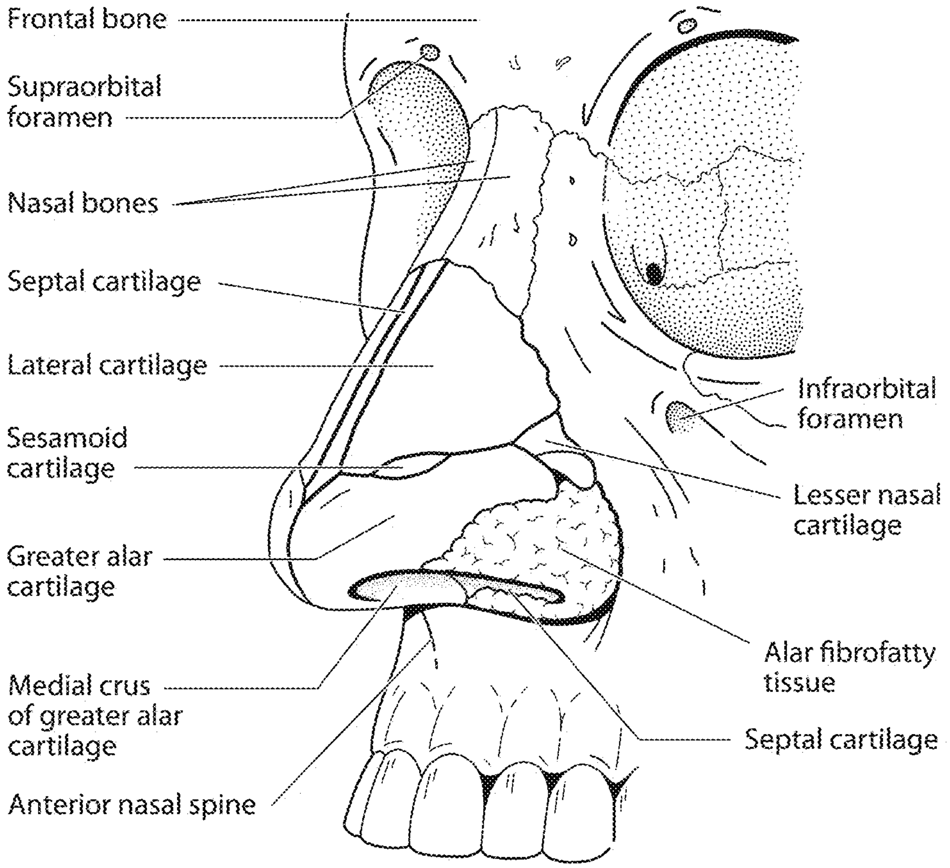

FIG. 2L shows an anterolateral view of a nose.

3.3 Patient Interface

Figure 3A:
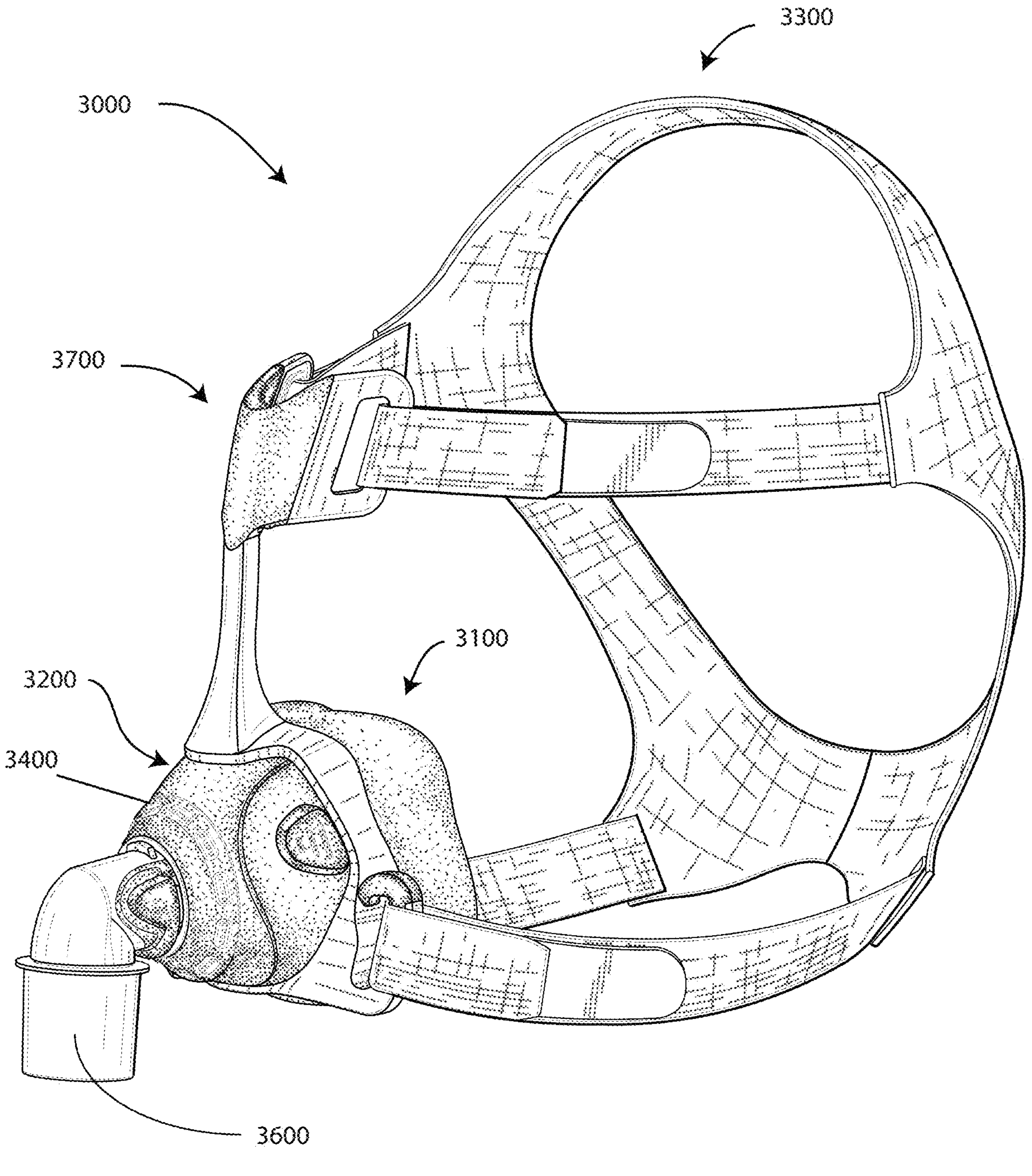

FIG. 3A shows a patient interface in the form of a nasal mask in accordance with one form of the present technology.

Figure 3B:
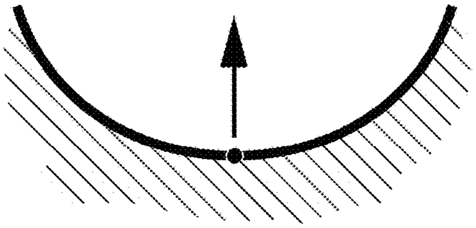

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
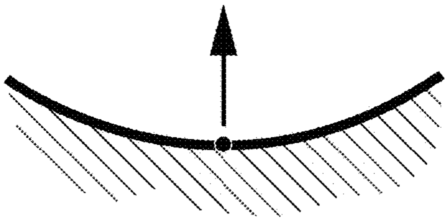

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
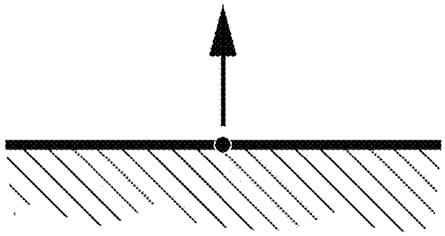

FIG. 3D shows a schematic of a cross-section through a structure at a point. An outward normal at the point is indicated. The curvature at the point has a value of zero.

Figure 3E:
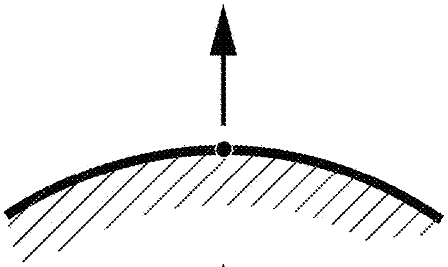

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
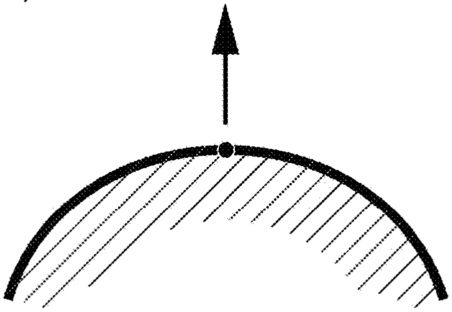

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3G:
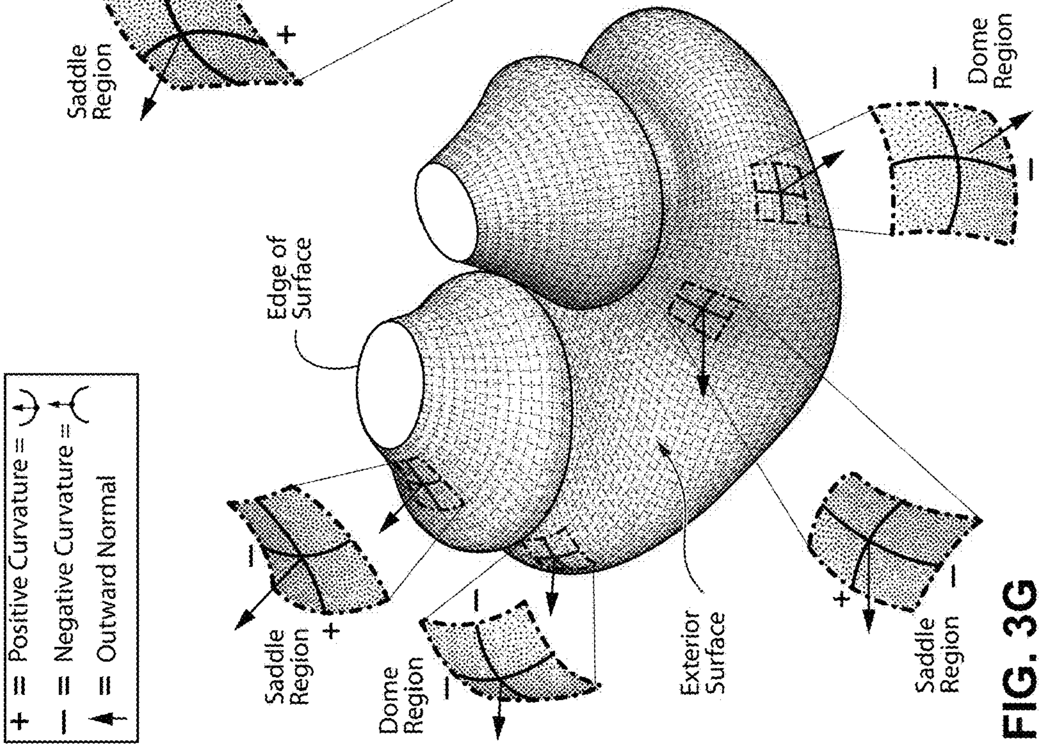

FIG. 3G shows a cushion for a mask that includes two pillows. An exterior surface of the cushion is indicated. An edge of the surface is indicated. Dome and saddle regions are indicated.

Figure 3H:
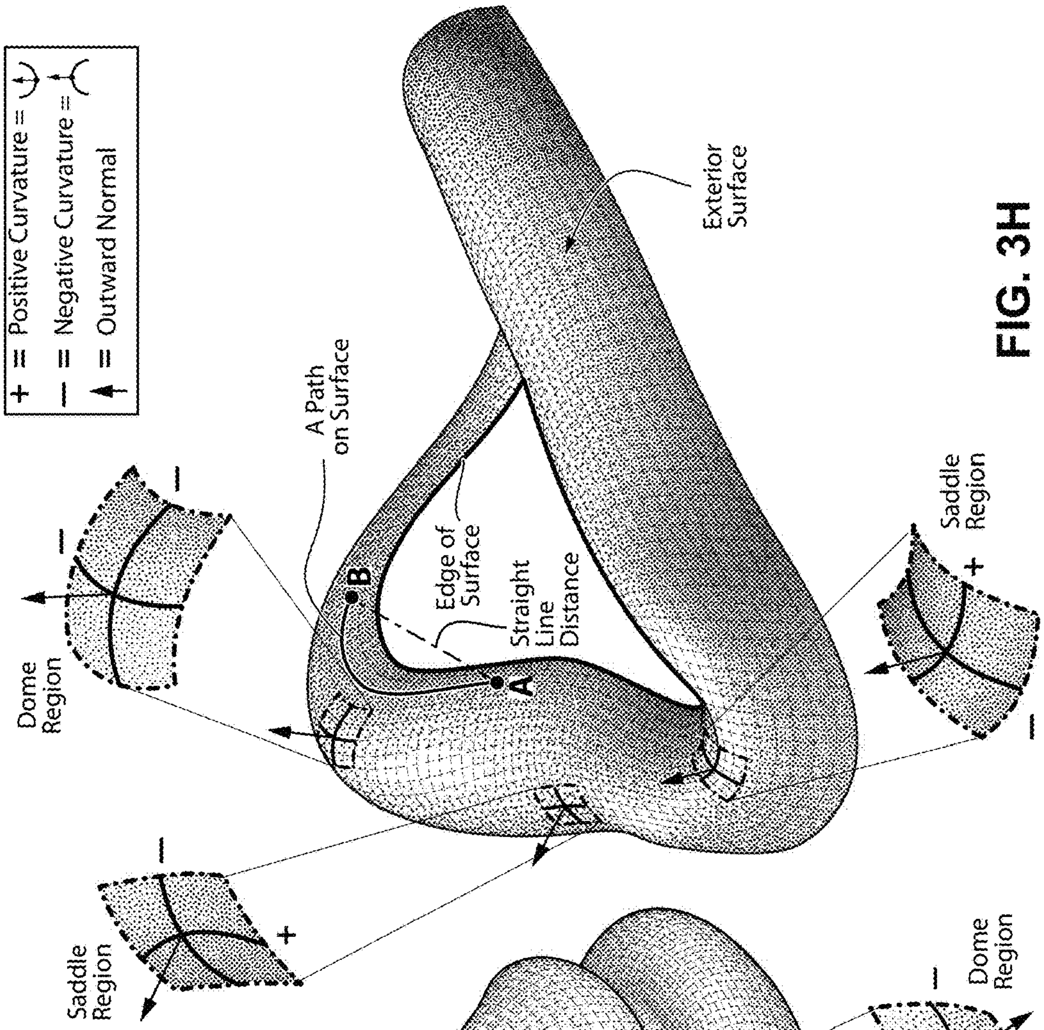

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
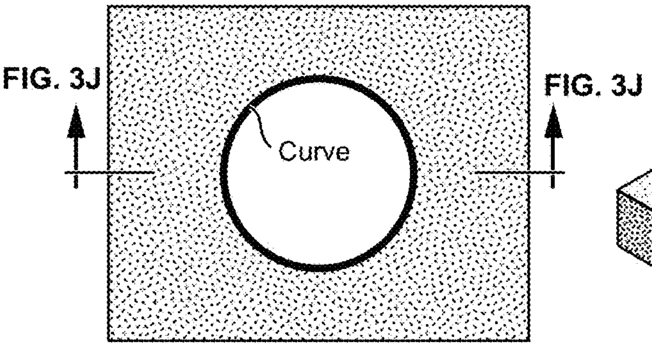

FIG. 3I shows the surface of a structure, with a one dimensional hole in the surface. The illustrated plane curve forms the boundary of a one dimensional hole.

Figure 3K:
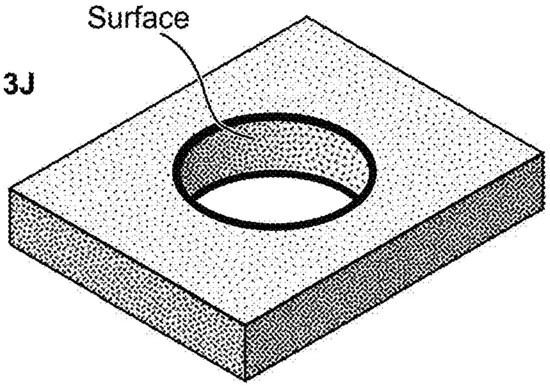
Figure 3J:
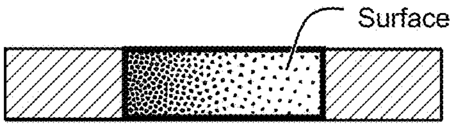

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
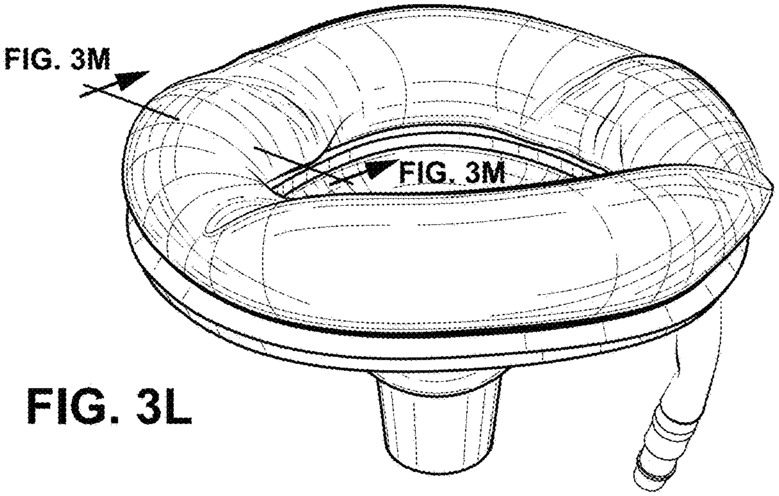

FIG. 3L shows a mask having an inflatable bladder as a cushion.

Figure 3M:
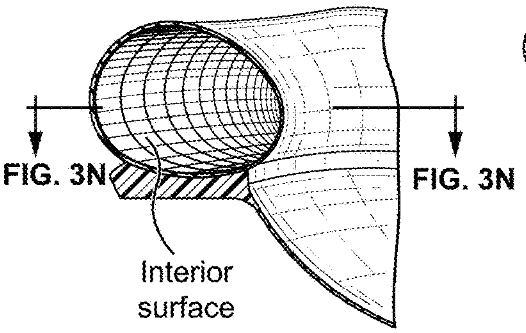

FIG. 3M shows a cross-section through the mask of FIG. 3L, and shows the interior surface of the bladder. The interior surface bounds the two dimensional hole in the mask.

Figure 3N:
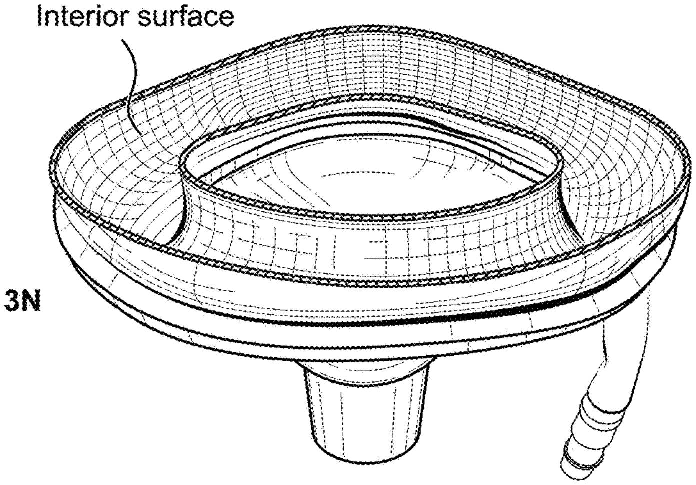

FIG. 3N shows a further cross-section through the mask of FIG. 3L. The interior surface is also indicated.

Figure 3O:
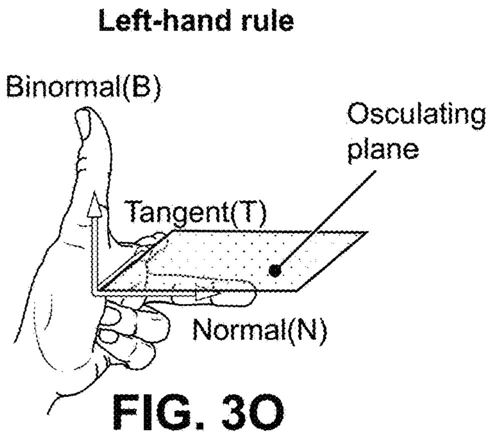

FIG. 3O illustrates a left-hand rule.

Figure 3P:
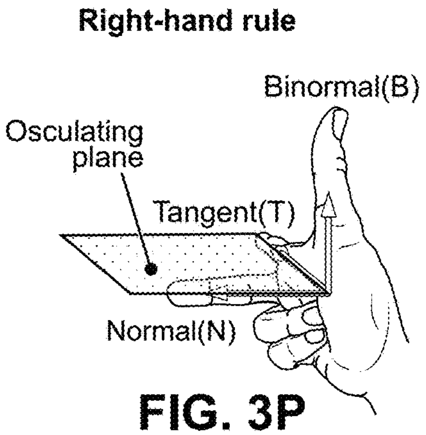

FIG. 3P illustrates a right-hand rule.

Figure 3Q:
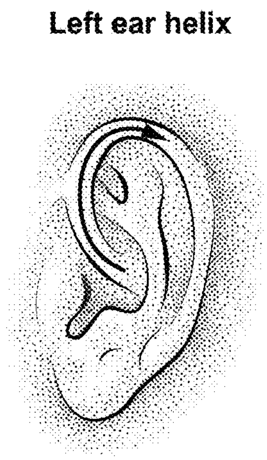

FIG. 3Q shows a left ear, including the left ear helix.

Figure 3S:
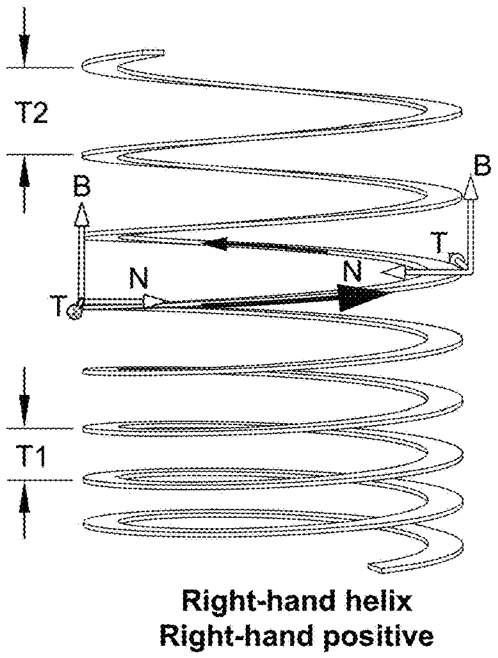
Figure 3R:
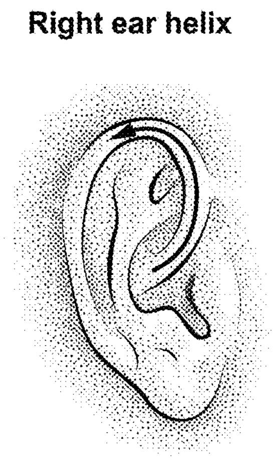

FIG. 3R shows a right ear, including the right ear helix.

FIG. 3S shows a right-hand helix.

Figure 3T:
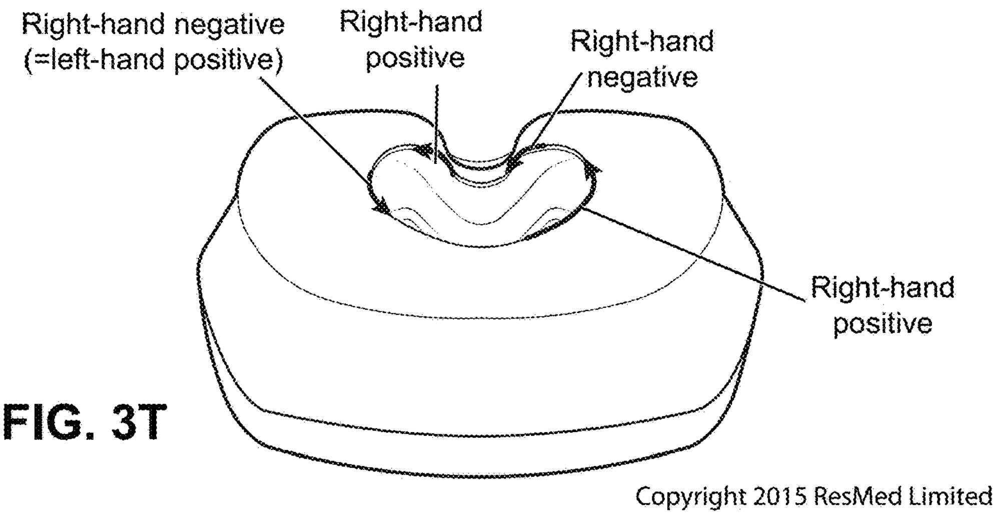

FIG. 3T shows a view of a mask, including the sign of the torsion of the space curve defined by the edge of the sealing membrane in different regions of the mask.

Figure 3U:
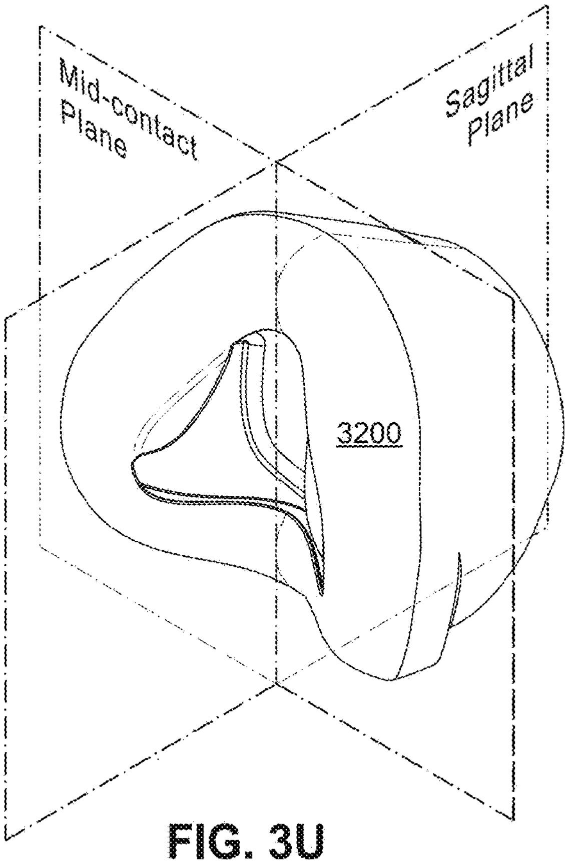

FIG. 3U shows a view of a plenum chamber 3200 showing a sagittal plane and a mid-contact plane.

Figure 3V:
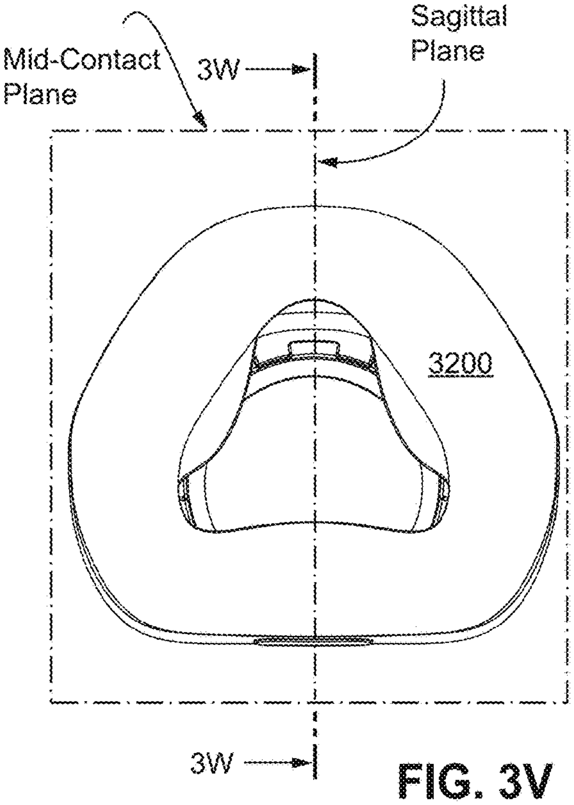

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
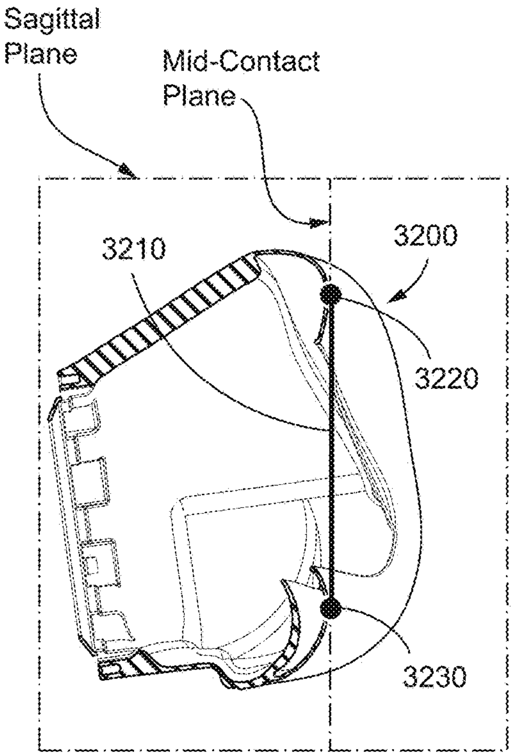

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
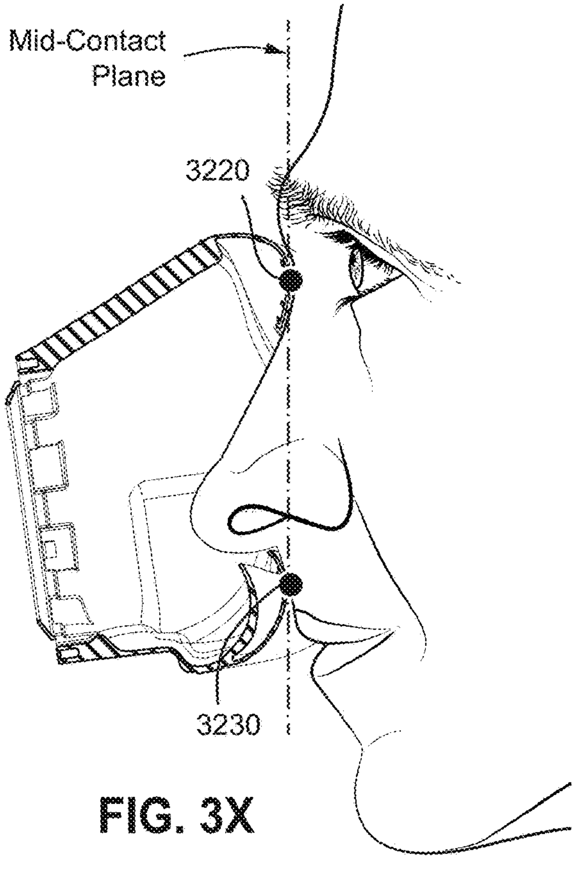

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

3.4 RPT Device

Figure 4A:
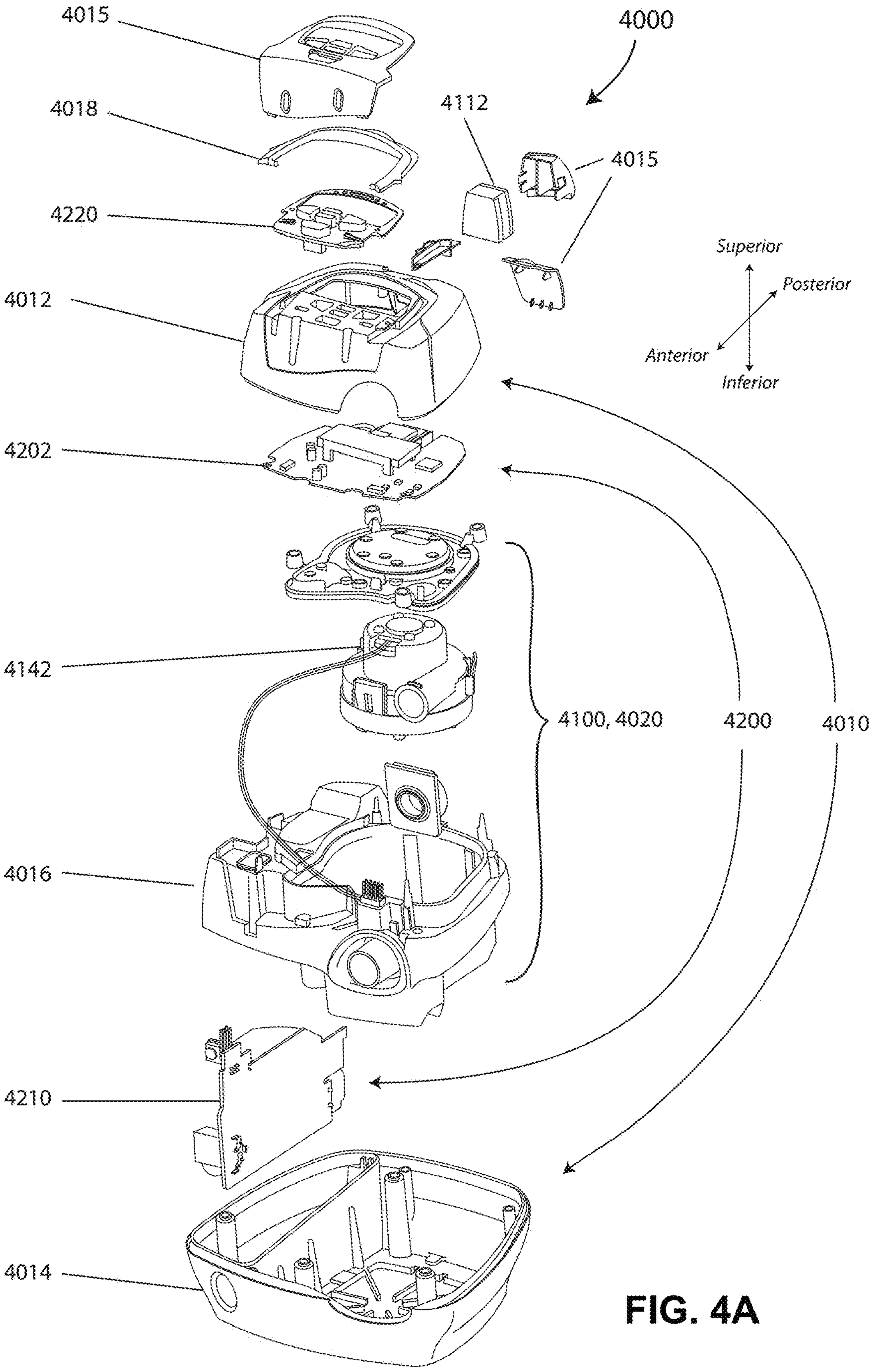

FIG. 4A shows an RPT device in accordance with one form of the present technology.

Figure 4B:
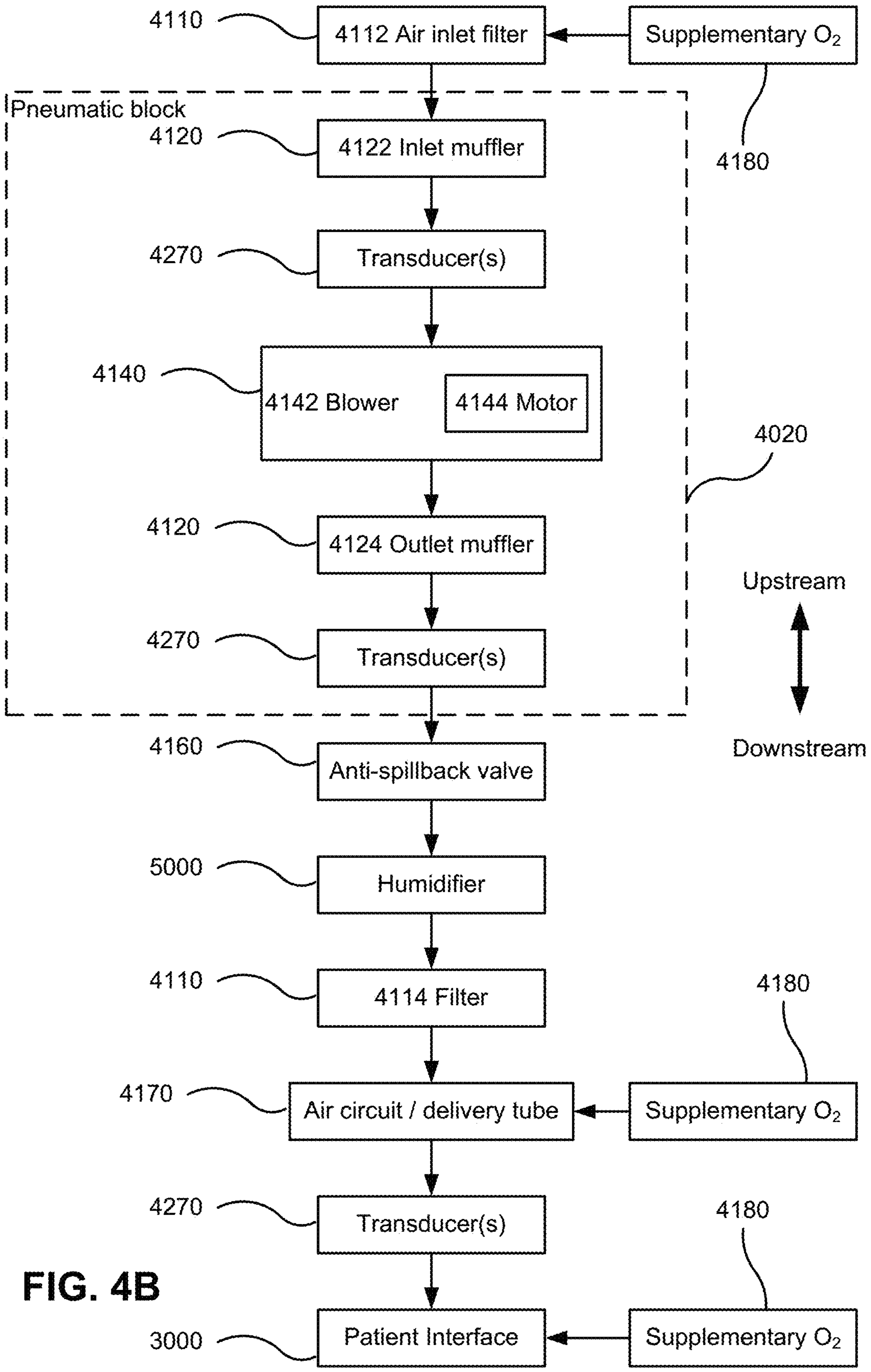

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
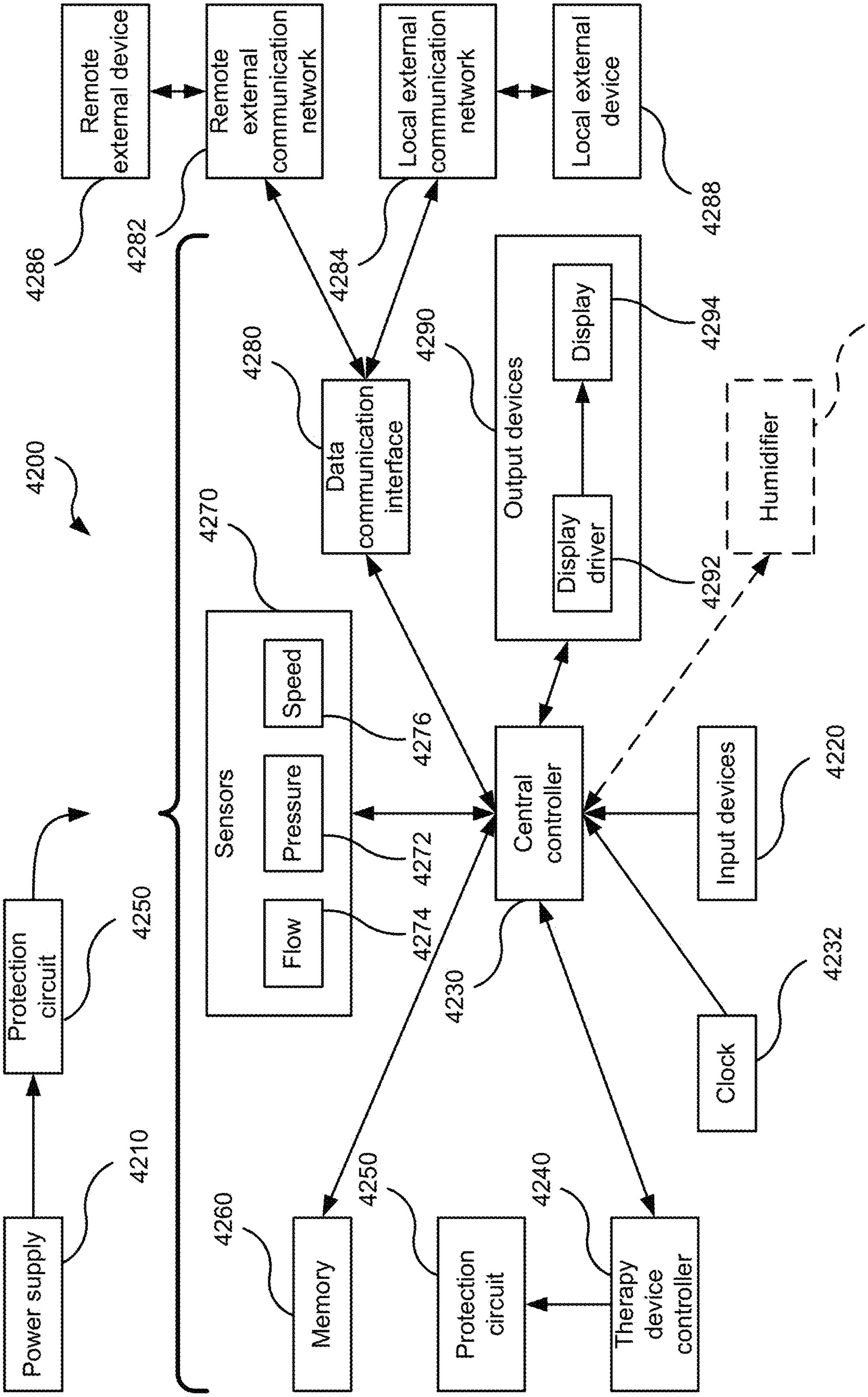

FIG. 4C is a schematic diagram of the electrical components of an RPT device in accordance with one form of the present technology.

Figure 4D:
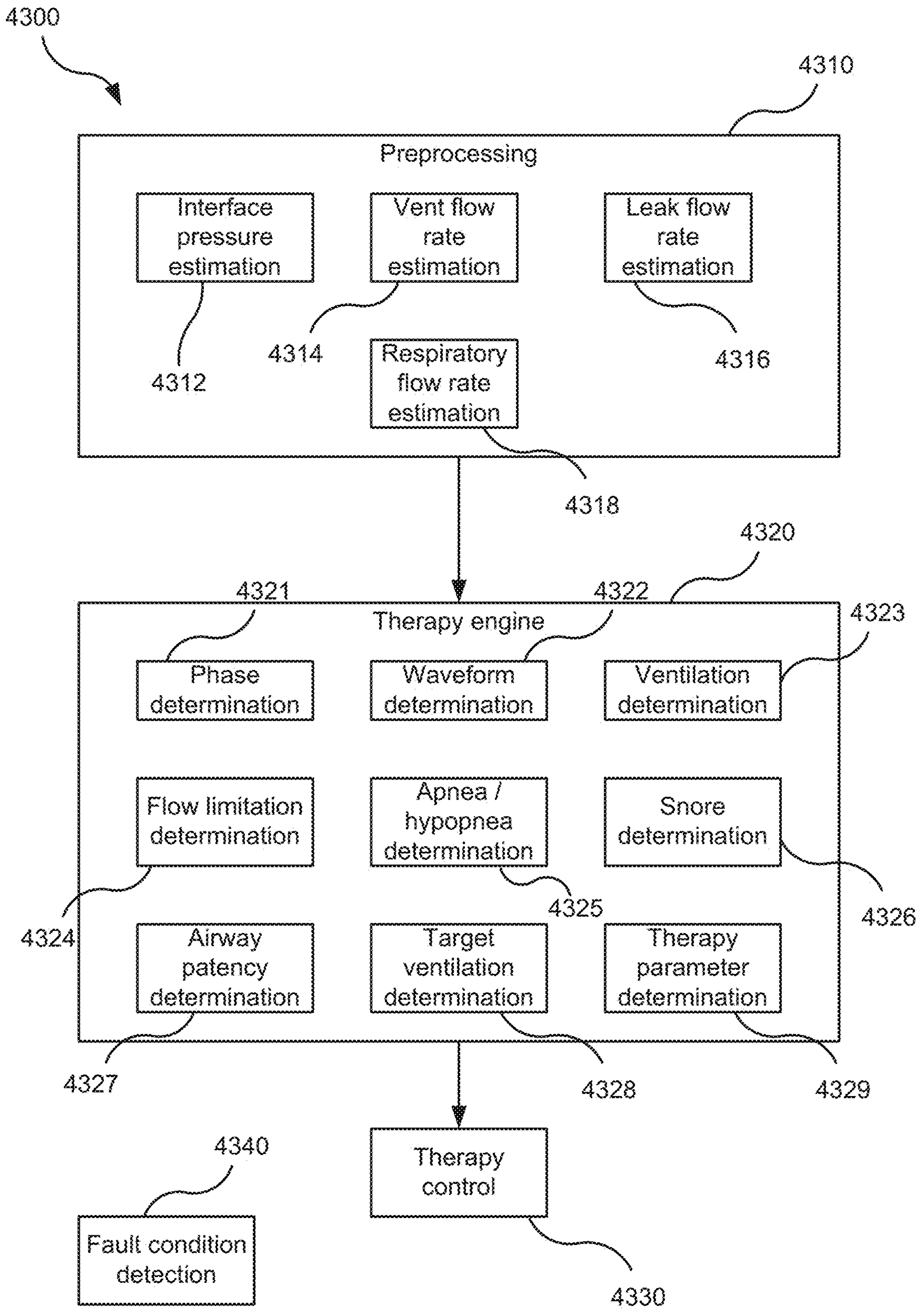

FIG. 4D is a schematic diagram of the algorithms implemented in an RPT device in accordance with one form of the present technology.

Figure 4E:
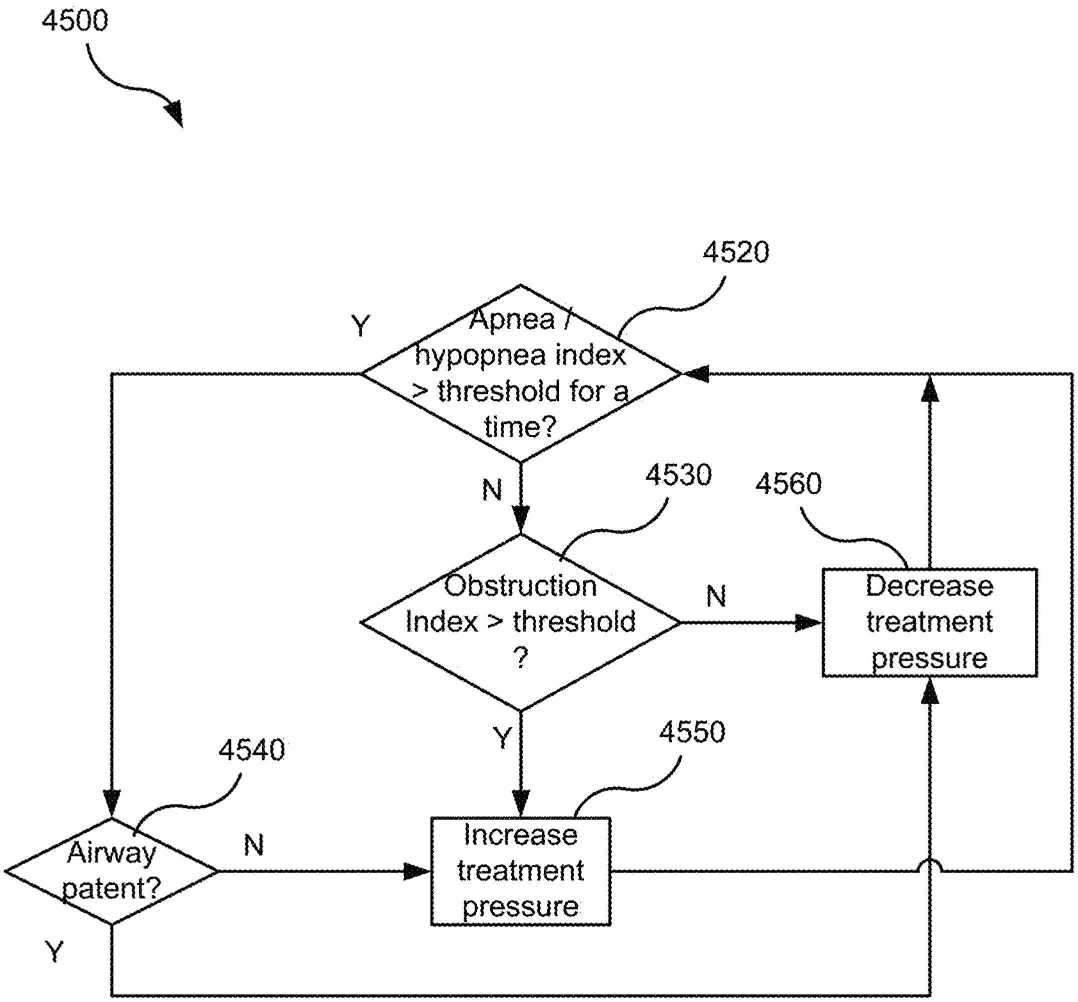

FIG. 4E is a flow chart illustrating a method carried out by the therapy engine module of FIG. 4D in accordance with one form of the present technology.

3.5 Humidifier

Figure 5A:
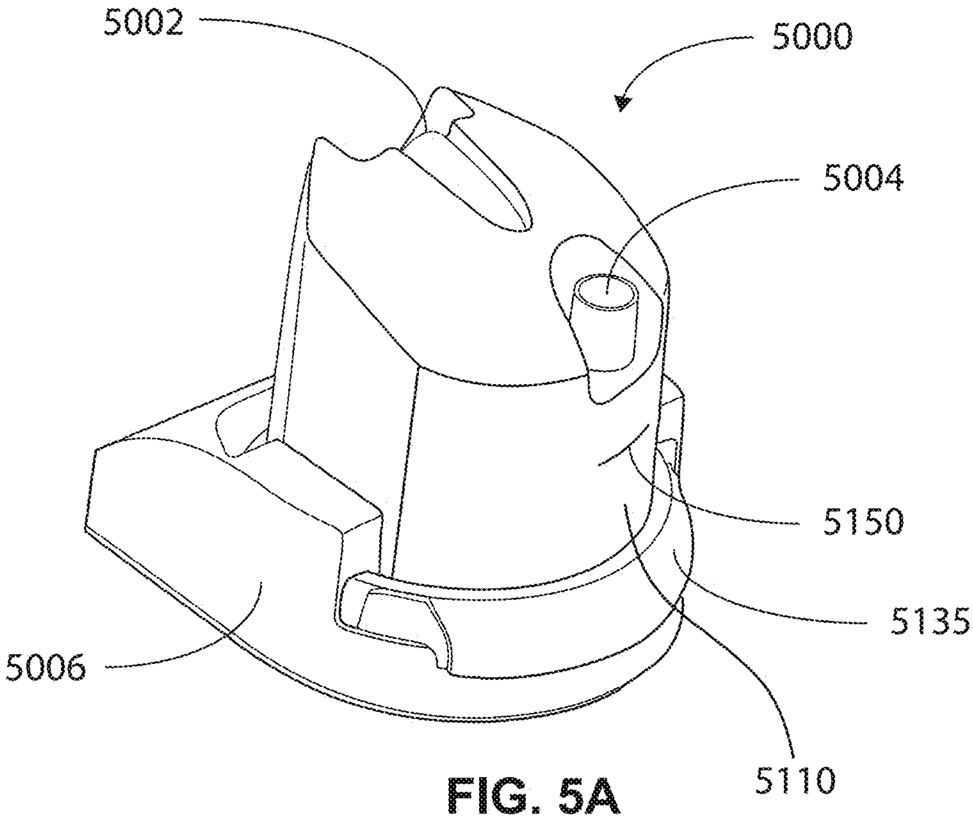

FIG. 5A shows an isometric view of a humidifier in accordance with one form of the present technology.

Figure 5B:
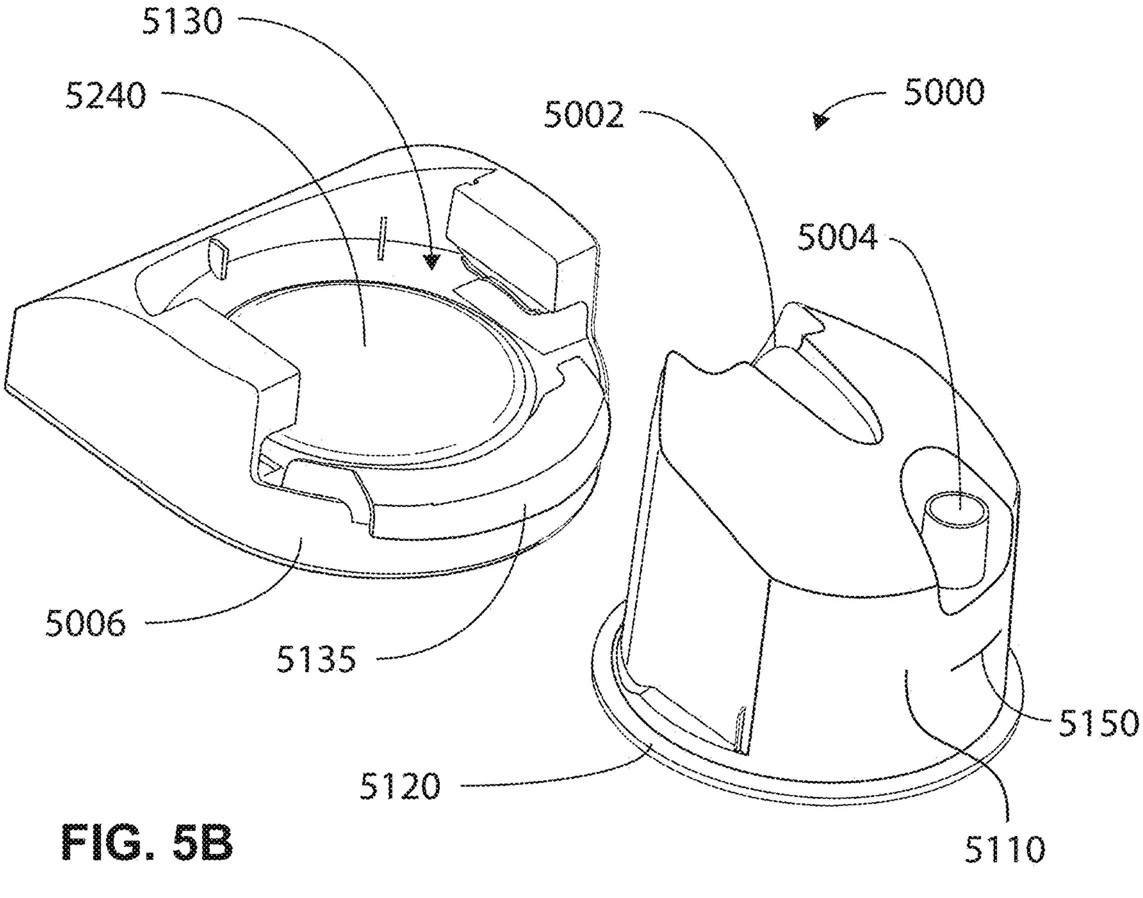

FIG. 5B shows an isometric view of a humidifier in accordance with one form of the present technology, showing a humidifier reservoir 5110 removed from the humidifier reservoir dock 5130.

Figure 5C:
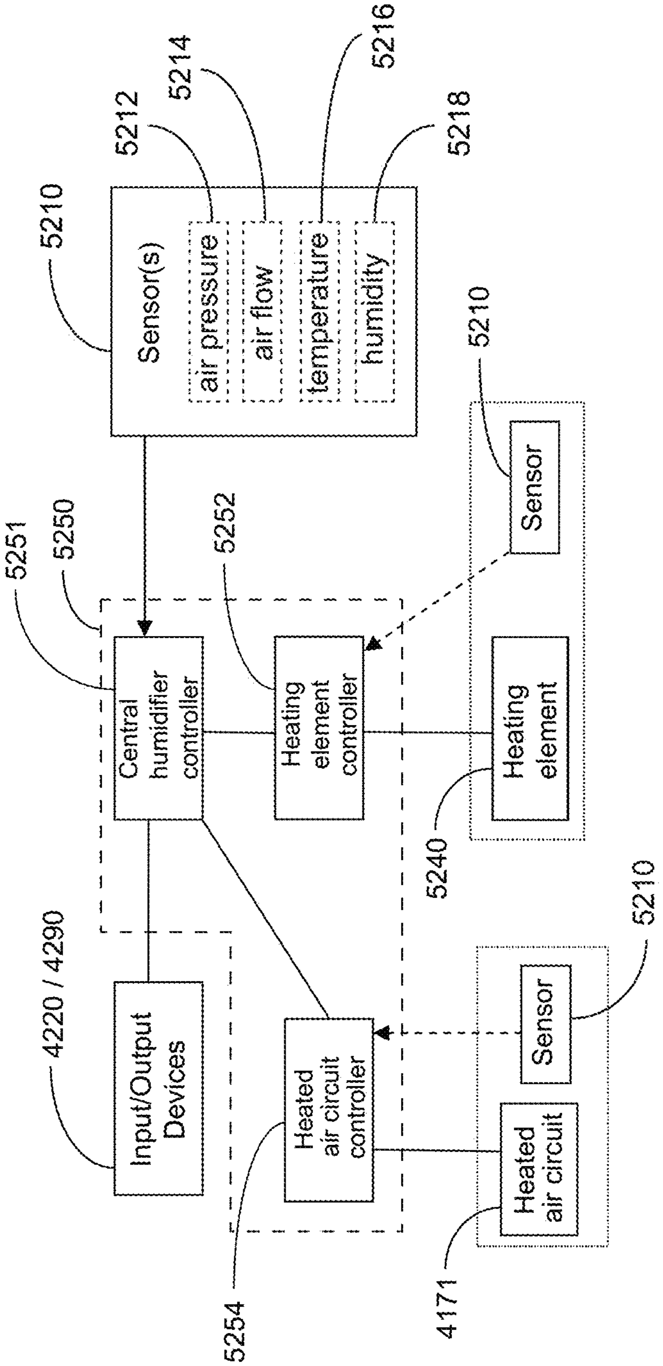

FIG. 5C shows a schematic of a humidifier in accordance with one form of the present technology.

3.6 Examples of the Present Technology

Figure 6A:
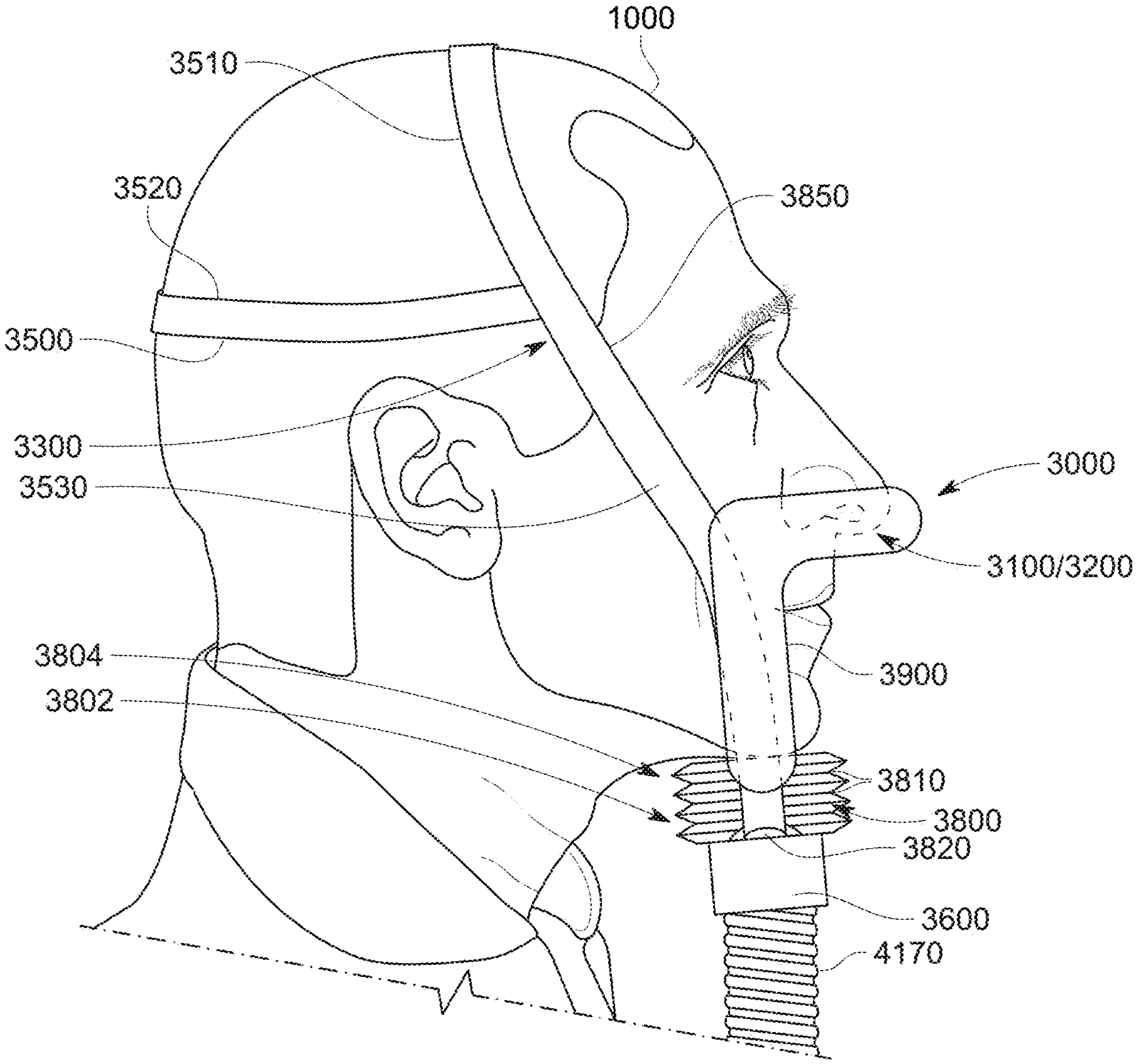

FIG. 6A shows a diagrammatic side view of a patient interface in use, in accordance with one form of the present technology.

Figure 6B:
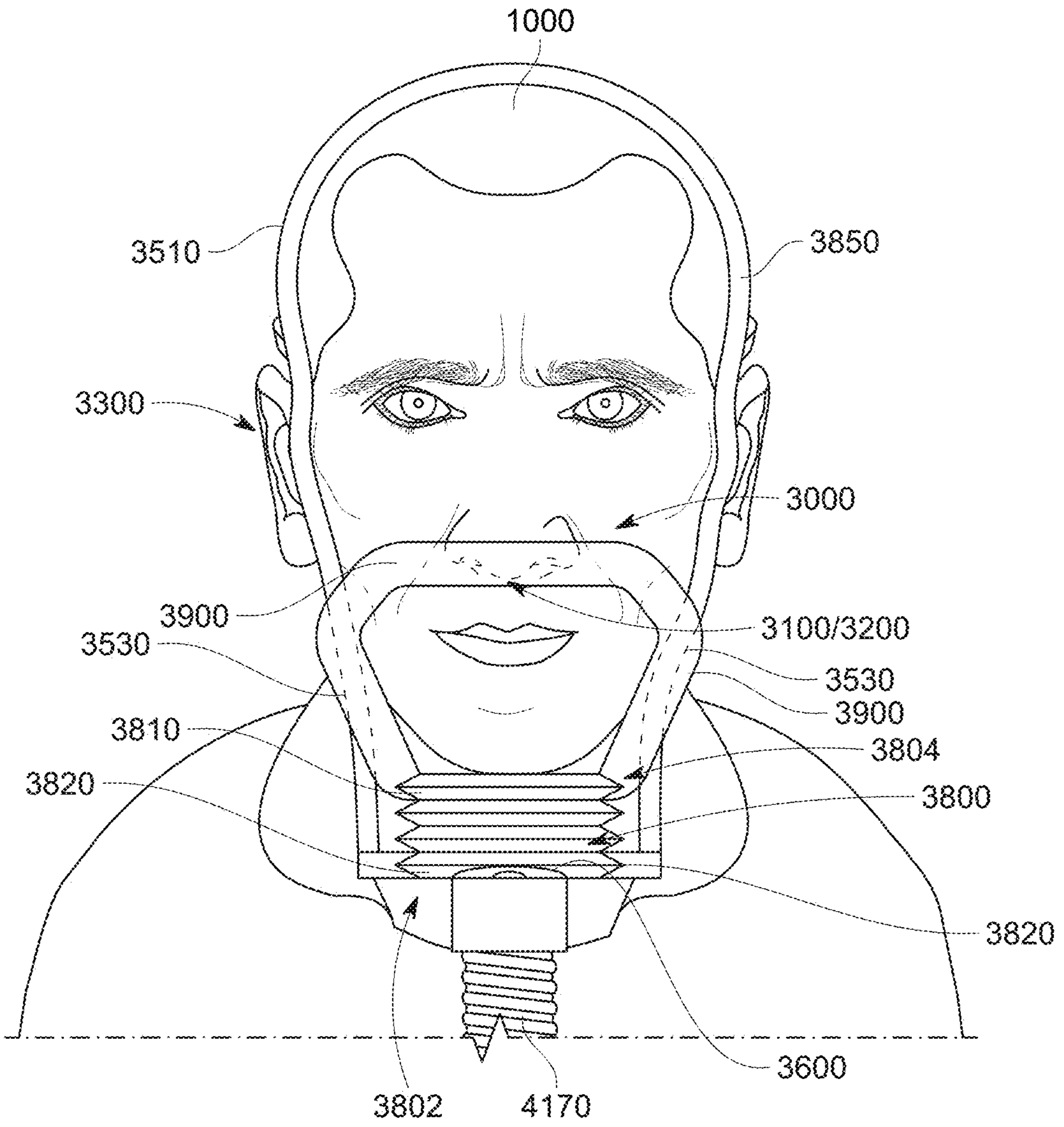

FIG. 6B shows a diagrammatic front view of the patient interface of FIG. 6A.

Figure 7:
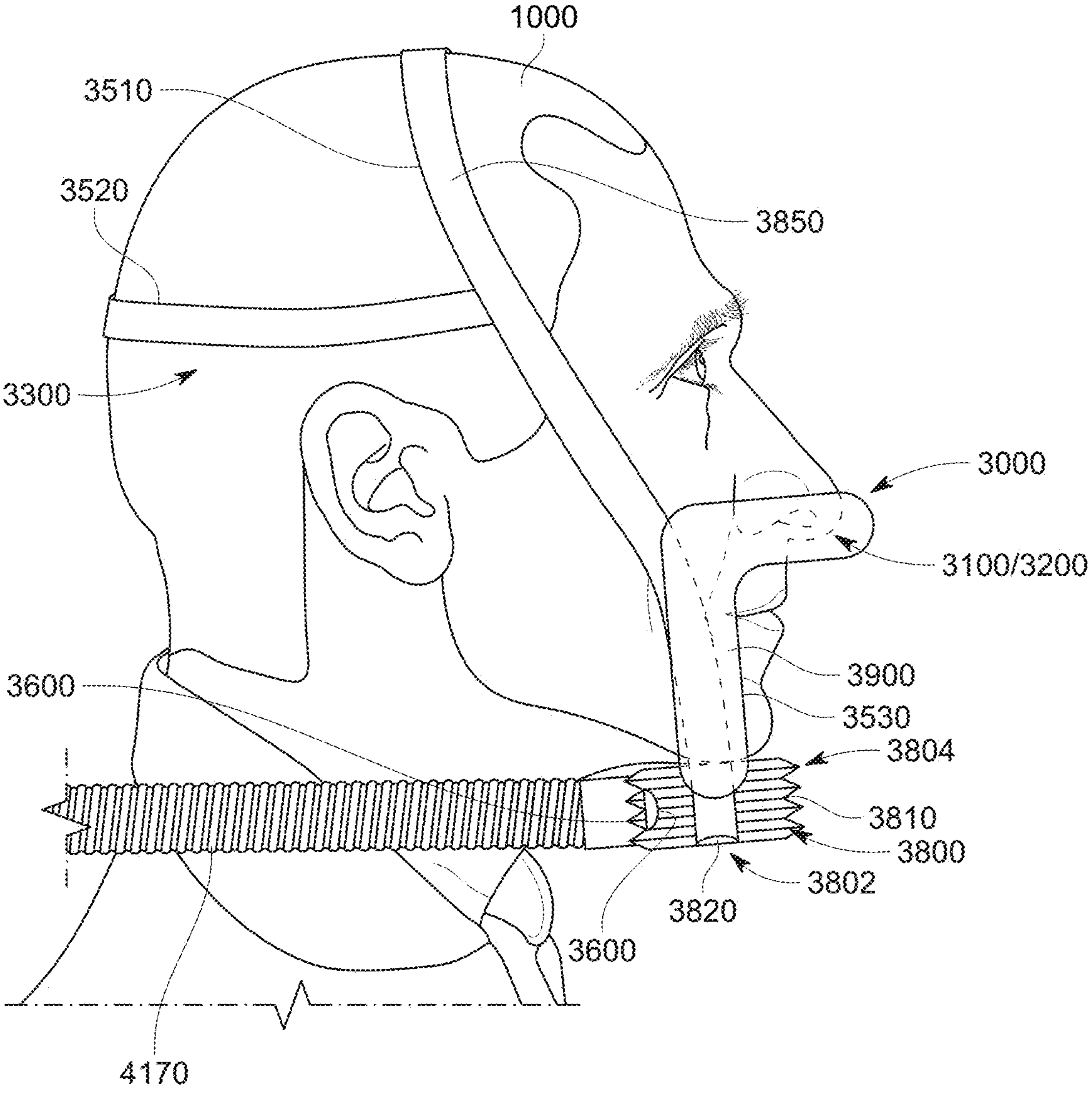

FIG. 7 shows a diagrammatic side view of a patient interface in use, in accordance with one form of the present technology.

Figure 8:
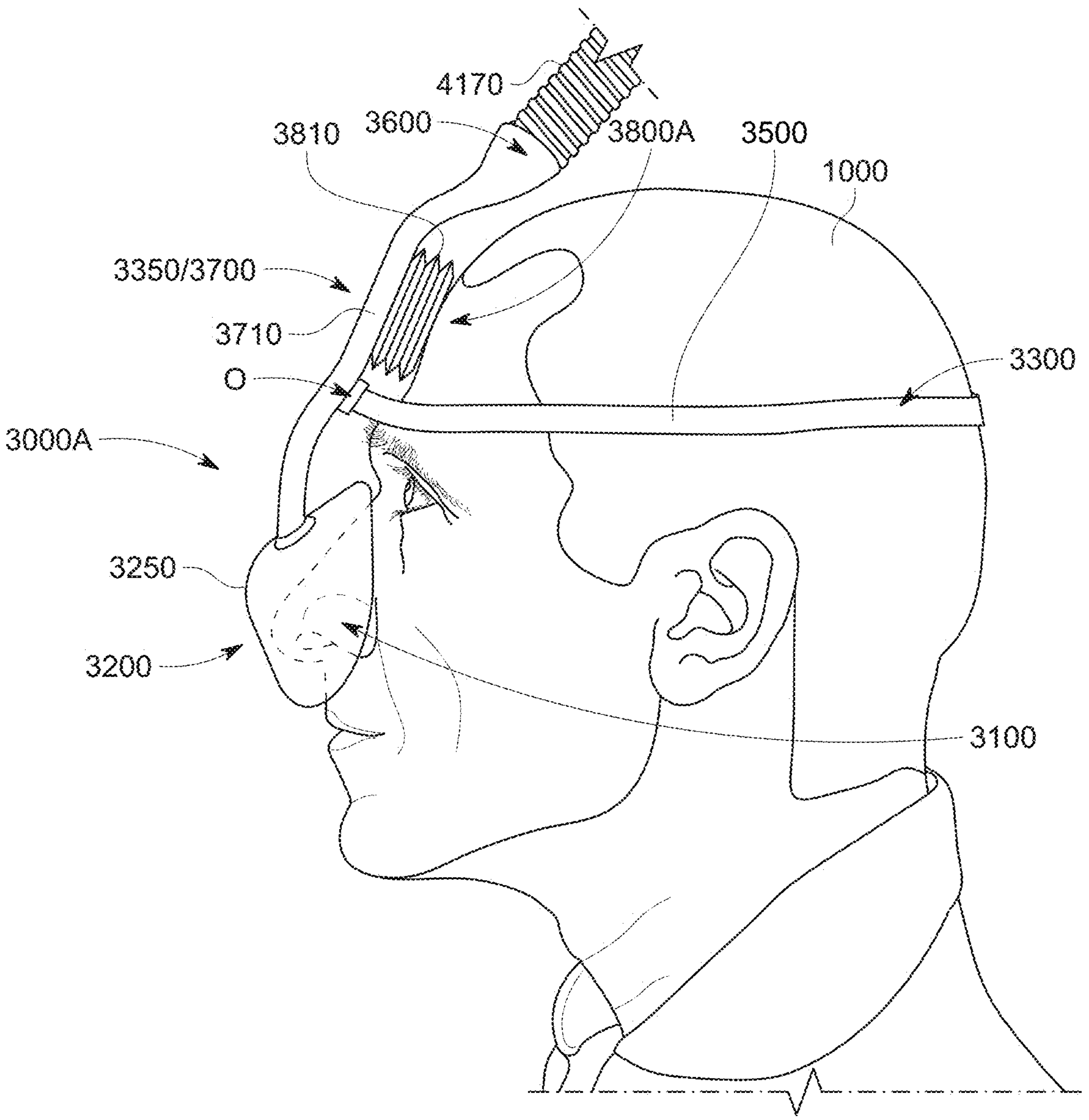

FIG. 8 shows a diagrammatic side view of a patient interface in use, in accordance with one form of the present technology.

Figure 9:
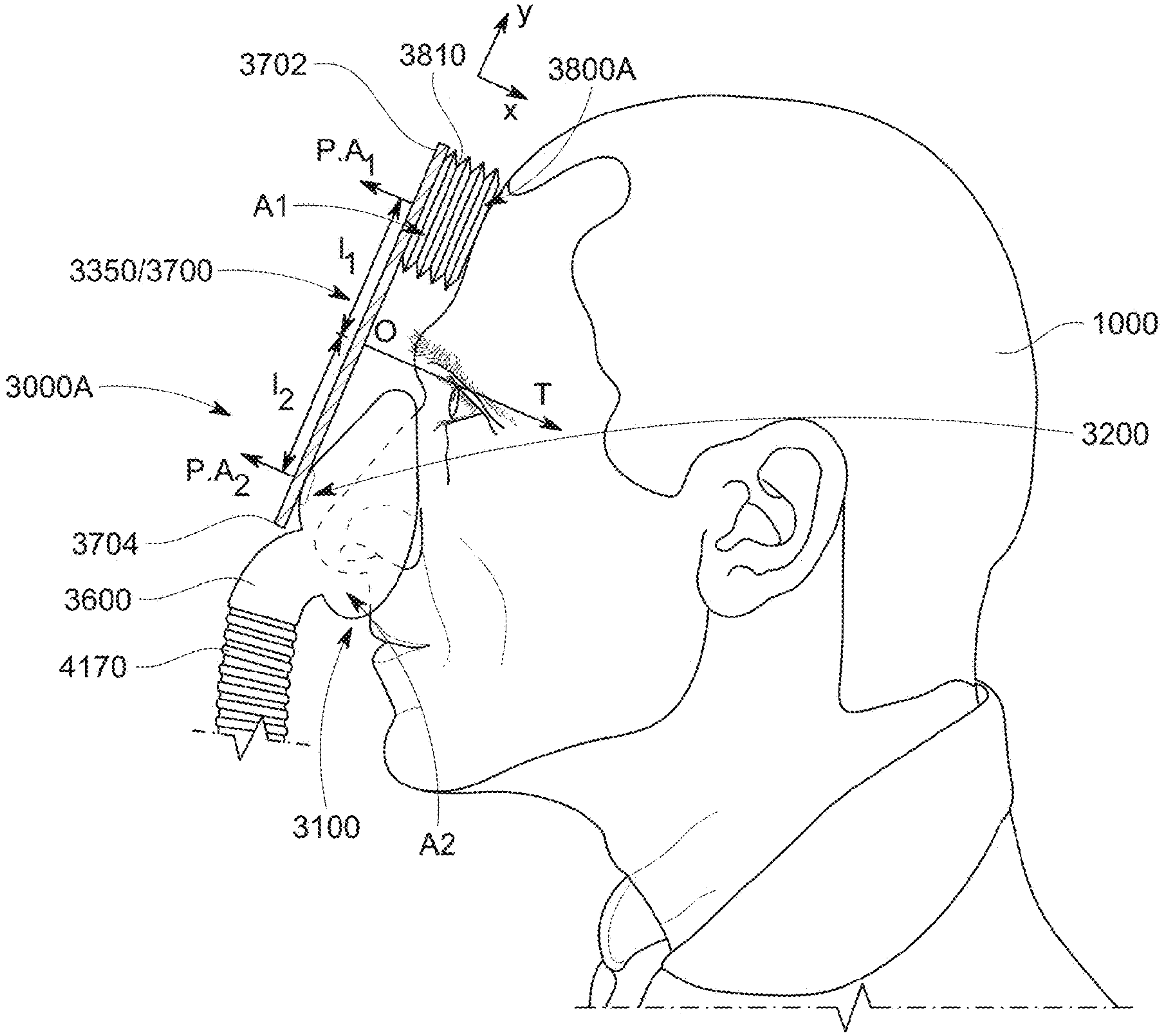

FIG. 9 shows a diagrammatic side view of a patient interface in use, in accordance with one form of the present technology, with headgear removed for clarity.

Figure 10:
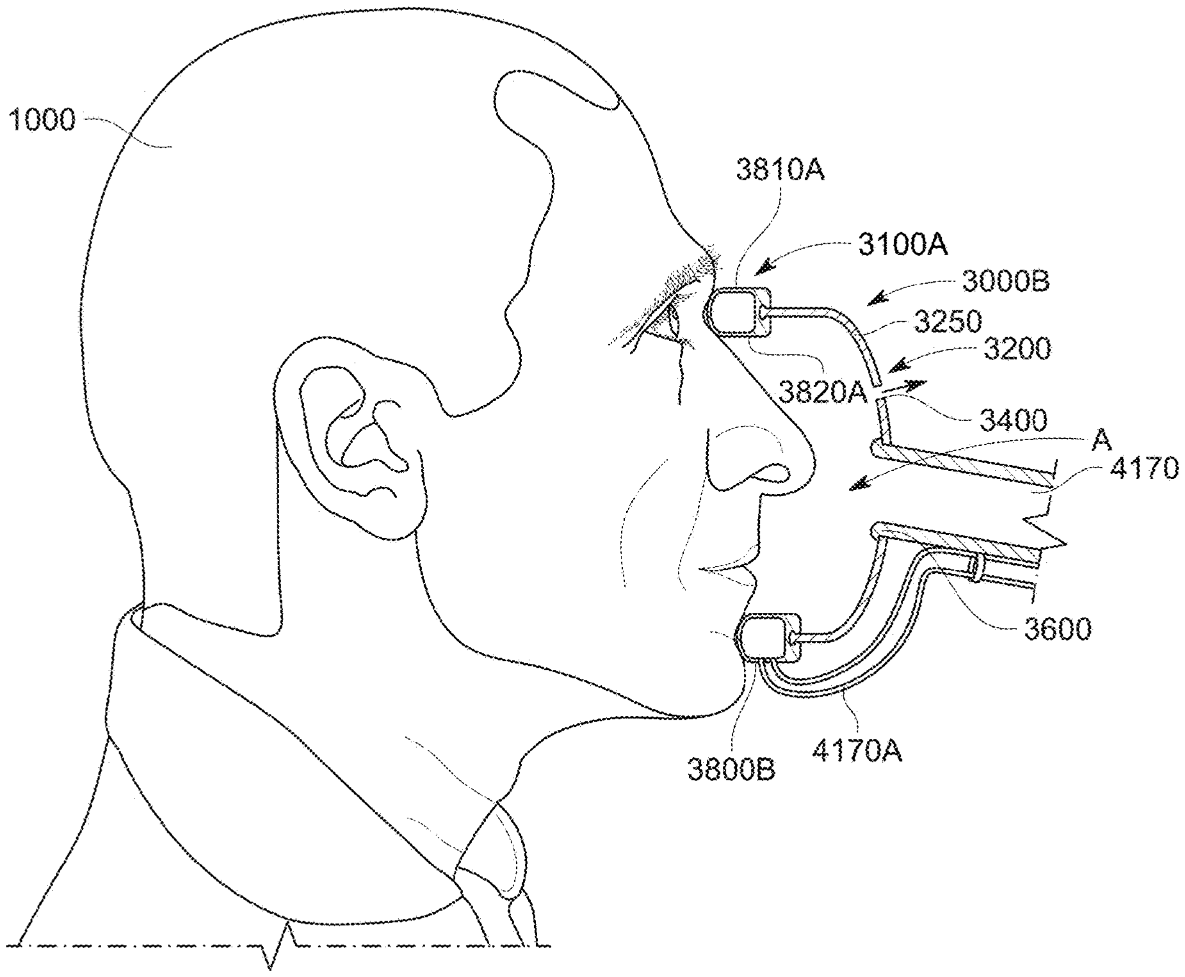

FIG. 10 shows a diagrammatic cross-sectional view through a section of a patient interface in use, in accordance with one form of the present technology, and with no headgear shown.

Figure 11:
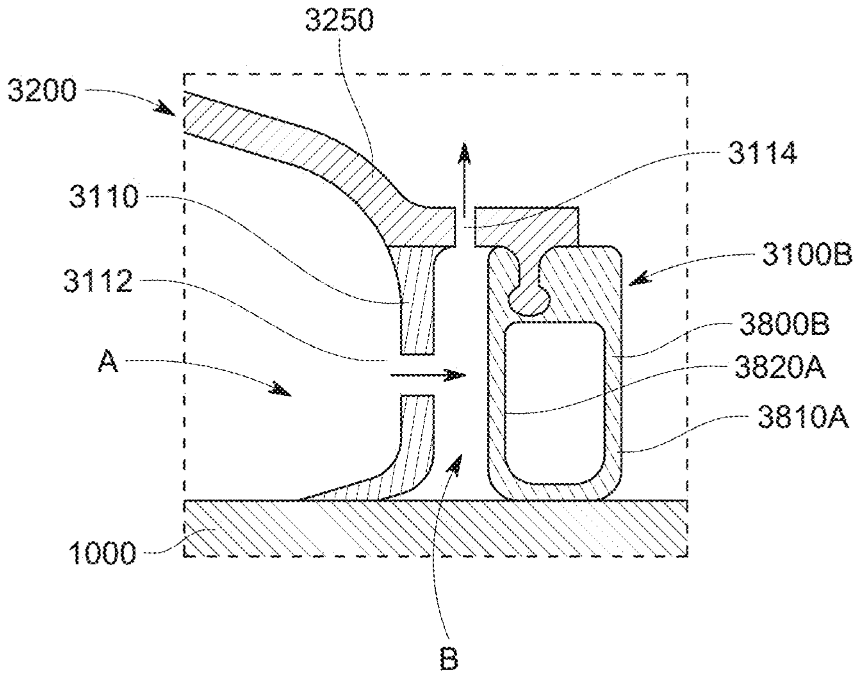

FIG. 11 shows an enlarged diagrammatic cross-sectional view through a section of a patient interface in use, in accordance with one form of the present technology.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

4.3 Patient Interface

A non-invasive patient interface 3000 in accordance with one aspect of the present technology is illustrated in FIG. 3A, and comprises the following functional aspects: a seal-forming structure 3100, a plenum chamber 3200, a positioning and stabilising structure 3300, a vent structure 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

Referring now to FIGS. 6A to 7 which illustrate examples of a patient interface 3000 in the form of a nasal mask. The example of FIG. 7 differs from that of FIGS. 6A and 6B only in the configuration of the connection port 3600.

The patient interface 3000 may comprise a seal-forming structure 3100, a plenum chamber 3200, and a positioning and stabilising structure 3300, and at least one inflatable body 3800.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O with respect to ambient.

4.3.1 Plenum Chamber

A patient interface 3000 according to some examples of the present technology comprises a plenum chamber 3200 pressurisable to a therapeutic pressure of at least 6 cmH2O above ambient air pressure. The plenum chamber 3200 may receive a flow of air at the therapeutic pressure for breathing by a patient.

In certain forms, the plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

In some forms, the plenum chamber 3200 is formed from a single homogeneous piece of material.

In certain forms of the present technology, the plenum chamber 3200 does not cover the eyes of the patient in use. In other words, the eyes are outside the pressurised volume defined by the plenum chamber 3200. Such forms tend to be less obtrusive and/or more comfortable for the wearer, which can improve compliance with therapy.

In certain forms of the present technology, the plenum chamber 3200 is constructed from a transparent material, e.g. silicone, a thermoplastic elastomer, a transparent polycarbonate or the like. The use of a transparent material can reduce the obtrusiveness of the patient interface 3000, and help improve compliance with therapy. The use of a transparent material can aid a clinician to observe how the patient interface 3000 is located and functioning.

In certain forms of the present technology, the plenum chamber 3200 is constructed from a translucent material. The use of a translucent material can reduce the obtrusiveness of the patient interface 3000, and help improve compliance with therapy.

In one form of the present technology, the plenum chamber 3200 comprises an inlet (not shown) configured to receive a flow of air at the therapeutic pressure for breathing by the patient. In some forms, the plenum chamber 3200 comprises a pair of inlets, configured to permit fluid communication with an interior of the plenum chamber 3200. For example, the plenum chamber 3200 comprises a pair of lateral inlets. However, the inlets may be formed in any other suitable location on the plenum chamber, e.g. on an anterior portion of the plenum chamber 3200.

4.3.2 Seal-Forming Structure

A patient interface 3000 according to some examples of the present technology comprises a seal-forming structure 3100 configured to form a seal in use with or around portions of the patient's nose. For example, the seal-forming structure 3100 is configured to form a seal in use with the underside of the patient's nose, around the patient's nares. In the illustrated example, the patient interface 3000 is in the form of a nasal mask. However, in other forms a patient interface 3000 in the form of a full-face mask or oro-nasal mask may be provided. In these forms, a seal-forming structure may be provided which is configured to form a seal in use with or around portions of the patient's mouth.

The seal-forming structure 3100 may be configured to maintain said therapeutic pressure in the plenum chamber 3200 throughout the patient's respiratory cycle in use.

The seal-forming structure 3100 may comprise at least one hole, or a pair of holes, neither of which are not shown in the figures, but which may be configured to allow a flow of air at therapeutic pressure to be delivered to the patient's nares. Each hole aligns in use with a respective nare of the patient. In some examples, the at least one hole is formed in a central portion of the seal-forming structure 3100. Each of the pair of holes may be provided by a nasal pillow.

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure 3300 and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

4.3.2.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure 3300.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

4.3.2.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

4.3.2.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

4.3.2.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

4.3.2.5 Forehead Region

In one form, the seal-forming structure that forms a seal in use on a forehead region of the patient's face. In such a form, the plenum chamber may cover the eyes in use.

4.3.2.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

4.3.3 Positioning and Stabilising Structure

The seal-forming structure 3100 of the patient interface 3000 of the present technology may be held in the sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus.

In one example, the positioning and stabilising structure 3300 comprises at least one strap 3500. The strap 3500 may have a rectangular cross-section. The strap 3500 may be a substantially flat strap 3500. However, the at least one strap 3500 may have any other suitably shaped cross-section.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap 3500. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises at least one strap 3500 constructed from a laminate of a fabric patient-contacting layer, a foam inner layer (not shown) and a fabric outer layer. In one form, the foam is porous to allow moisture, (e.g., sweat), to pass through the strap 3500. In one form, the fabric outer layer comprises loop material portion to engage with a hook material portion.

The strap 3500 length may be adjusted to adjust the headgear forces provided by the positioning and stabilising structure 3300.

In certain forms of the present technology, a positioning and stabilising structure 3300 comprises a strap 3500 that is extensible, e.g. resiliently extensible. For example the strap 3500 may be configured in use to be in tension, and to direct a force to draw a seal-forming structure 3100 into sealing contact with a portion of a patient's face. In an example the strap 3500 may be configured as a tie.

In certain forms of the present technology, a positioning and stabilising structure 3300 comprises a strap 3500 that is bendable and e.g. non-rigid. An advantage of this aspect is that the strap 3500 is more comfortable for a patient to lie upon while the patient is sleeping.

In certain forms of the present technology, a positioning and stabilising structure 3300 comprises a strap 3500 constructed to be breathable to allow moisture vapour to be transmitted through the strap 3500.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another suitable for a small sized head, but not a large sized head.

As is perhaps best illustrated in FIGS. 6A to 7, the positioning and stabilising structure 3300 may comprise a portion which extends in use over the top of the patient's head, e.g. a top strap 3510, and reference herein will be made as such. The positioning and stabilising structure 3300 may comprise a portion which extends in use around the rear of the patient's head, e.g. a rear strap 3520, and reference herein will be made as such. The positioning and stabilising structure 3300 may comprise a portion which extends in use below the patient's chin and/or lower jaw region, e.g. a chin strap 3530, and reference herein will be made as such.

The chin strap 3530 may be connected to at least one of the top strap 3510 and the rear strap 3520. In some forms, the chin strap 3530 may form part of the top strap 3520. For example, the chin strap 3530 and the top strap 3510 may form a single strap, as illustrated. The rear strap 3520 may be connected to this single strap, as illustrated, or it may be integrally formed with the single strap in other forms.

At least one of the chin strap 3530, the top strap 3510 and the rear strap 3520 extends in use over a side region of the patient's face. As illustrated, portions of the chin strap 3530, the top strap 3510 and the rear strap 3520 extend in use over side regions of the patient's face.

4.3.4 Inflatable Body

According to an aspect of the present technology, the patient interface 3000 may comprise at least one inflatable body 3800.

The inflatable body 3800 may be inflated with a fluid, e.g. a gas or a liquid. In the illustrated embodiment, the inflatable body 3800 may be inflated by a pressurised gas which is breathable.

The inflatable body 3800 may be configured to expand and compress. For example, the inflatable body 3800 may be substantially hollow, and the inflatable body 3800 may be formed from a soft, flexible material, e.g. silicone. This may allow the inflatable body 3800 to expand as it is inflated, and compress as it is deflated. Inflation may occur as the internal pressure of the inflatable body 3800 is increased, and deflation may occur as the internal pressure of the inflatable body 3800 is decreased.

The inflatable body 3800 may be configured to facilitate expansion and compression of the inflatable body 3800. The inflatable body 3800 may be in the form of a bellows. The inflatable body 3800 may comprise one or more folds 3810 and/or thinned regions (not shown). The folds 3810 and/or thinned regions may facilitate expansion and compression of the inflatable body 3800 so that the size of the inflatable body 3800 may be increased or decreased.

As described herein, the patient interface 3000 may comprise a connection port 3600 which is configured to receive a supply of pressurised breathable gas. For example, the inflatable body 3800 may comprise an inlet configured to receive a supply of fluid, e.g. the supply of pressurised gas. The inlet may act as the connection port 3600. Therefore, the pressurised gas may be supplied to the inflatable body 3800 by an air circuit 4170 as described herein, e.g. an air delivery conduit, via the connection port 3600.

The inflatable body 3800 that receives the supply of pressurised gas as described above may be fluidly connected to the plenum chamber 3200. For example, the patient interface 3000 may comprise at least one conduit 3900, preferably a pair of conduits 3900, which fluidly connect the inflatable body 3800 to the plenum chamber 3200. The conduit(s) 3900 may be positioned in use on the patient's head and/or face, as illustrated. The conduit(s) 3900 may be releasably or permanently attached to at least one of the plenum chamber 3200 and the inflatable body 3800. The plenum chamber 3200 may comprise inlets which are not shown but have been described above, to permit the passage of the breathable pressurised gas into the plenum chamber 3200 from the conduit(s) 3900. The inflatable body 3800 may comprise one or more outlets (not shown) to permit the passage of the breathable pressurised gas out from the inflatable body 3800 and into the plenum chamber 3200.

The at least one inflatable body 3800 may be provided as part of the positioning and stabilising structure 3300. However, in other forms, the at least one inflatable body 3800 may not be provided as part of the positioning and stabilising structure 3300. For example, the patient interface 3000 may comprise a chin portion as described herein, e.g. a chin strap, but the chin portion may connect to the plenum chamber, frame and/or seal-forming structure, or to another component which is attached to or formed with the plenum chamber and/or seal-forming structure. In examples, the patient interface may also comprise a top strap or portion, and the top strap and chin portion may effectively be connected together by the plenum chamber, frame and/or seal-forming structure to form a hoop structure as described herein.

At least one inflatable body 3800 may be located in use proximate at least one region of the patient's head and/or face. In one form, one inflatable body 3800 may be located in use proximate one region of the patient's head and/or face, as illustrated. For example, one inflatable body 3800 may be located in use below the patient's chin and/or lower jaw region, as illustrated. However, in other forms, a plurality of inflatable bodies 3800 may be located in use proximate regions of the patient's head and/or face.

In one form, the inflatable body 3800 may be provided to the chin strap 3530. The inflatable body 3800 may form part of the chin strap 3530. In these forms, the inflatable body 3800 may engage in use with the patient's chin and/or lower jaw region when the inflatable body 3800 is inflated. As illustrated, the inflatable body 3800 may be positioned in use between the patient's chin and/or lower jaw region and the chin strap 3530. This may be used to tension or tighten the chin strap 3530 as will be described in more detail below.

However in other forms not shown, the inflatable body 3800 may be provided to or form part of another portion of the positioning and stabilising structure 3300, e.g. to the top strap 3510 so that it is located in use on top of the patient's head. In these forms, the chin strap 3530 as described herein, may engage in use with the patient's chin and/or lower jaw region when the inflatable body 3800 is inflated. Therefore, in these forms, the inflatable body 3800 can be positioned in use between the top of the patient's head and the top strap 3510. This may be used to tension or tighten the top strap 3510.

In yet other forms not shown, the inflatable body 3800 may be positioned in use between the back of the patient's head and the rear portion as described herein. Therefore, the inflatable body 3800 may be positioned in use between the back of the patient's head and the rear strap 3520. This may be used to tension or tighten the rear strap 3520.

The inflatable body 3800 may be releasably or permanently attached to the patient interface 3000. For example, the inflatable body 3800 may be releasably or permanently attached to the positioning and stabilising structure 3300, e.g. the top strap 3510 and/or the chin strap 3530. However in other forms already described the inflatable body 3800 may be releasably or permanently attached to the chin portion, e.g. the chin strap, which does not form part of the positioning and stabilising structure 3300.

A releasable attachment may be preferred as it may allow the inflatable body 3800 to be selectively removed from the positioning and stabilising structure 3300 and these components may then be cleaned or replaced more easily.

The positioning and stabilising structure 3300 may connect to the inflatable body 3800 at a connection point 3820. For example, the chin strap 3530 may connect to the inflatable body 3800 at the connection point 3820.

The connection point 3820 may be located in a region of the inflatable body 3800 which permits it to inflate and expand in use in a direction extending away from the connection point 3820 and towards the patient's head. For example, the connection point 3820 may be located on an inferior region 3802 of the inflatable body 3800 located in use under the patient's chin and/or lower jaw region, as illustrated. In other forms described above but that are not shown, the inflatable body 3800 may connect to a chin portion as described herein, e.g. a chin strap, which does not form part of the positioning and stabilising structure 3300 at a connection point similar to connection point 3820.

In examples (not shown) where the inflatable body 3800 is located on top of the patient's head, a connection point may be located on a superior region of the inflatable body 3800.

The positioning and stabilising structure 3300 may be structured and arranged to be tensioned or tightened on the patient's head. The inflatable body 3800 may facilitate this. A first region of the inflatable body 3800 contacts in use a region of the patient's head, and the connection point 3820 may be pushed further away from the patient's head as the inflatable body 3800 expands. For example, a superior region 3804 of the inflatable body 3800 contacts in use a region of the patient's head under the patient's chin and/or lower jaw region, and as the connection point 3820 is pushed further away from the patient's head by the expansion of the inflatable body 3800, the chin strap 3530 may become tensioned or tightened. As a result, the positioning and stabilising structure 3300 may be tensioned or tightened on the patient's head by the expansion of the inflatable body 3800.

This may provide a number of benefits which will become more apparent from the discussion below.

One such benefit is that the patient interface may be configured to limit or prevent mouth leak or mandible movement during CPAP therapy.

The inflatable body 3800 may facilitate this. For example, the inflatable body 3800 may create in use a chin strap force which acts on the patient's chin and/or lower jaw region to help maintain the patient's mouth in a closed position. The chin strap force may extend towards the region under the patient's chin and/or lower jaw region. Therefore, the chin strap force may extend in a direction which is substantially parallel to the coronal plane (shown in FIG. 2E).

As the inflatable body 3800 is inflated, the chin strap force is increased. As described above, the chin strap 3530 becomes tensioned or tightened as the inflatable body 3800 is inflated. Tensioning or tightening of the chin strap 3530 may increase the chin strap force to help maintain the patient's mouth in a closed position, and as a result it can limit or prevent mouth leak or mandible movement during CPAP therapy.

In other forms not shown, the chin portion may be in the form of a sling for the patient's chin. The top portion which may be in the form of a top strap, for example, may be attached to the sling such that the top portion loops from one side of the sling, over the top of the patient's head to the opposite side of the sling. The inflatable body 3800 as described herein may be provided to at least one of the sling and the top portion. This arrangement may be used with a nasal mask as described herein, or other existing nasal masks. This arrangement can be used to help limit or prevent mouth leak or mandible movement during CPAP therapy when using such nasal masks.

Therefore, in some forms, the chin portion, e.g. chin strap 3530, and the top portion, e.g. the top strap 3510, may form a hoop structure 3850 which loops arounds the patient's head. The inflatable body 3800 may be attached to or formed with a portion of the hoop structure 3850. The hoop structure 3850 may form part of the patient interface 3000, e.g. the positioning and stabilising structure 3300, as illustrated. However, it is to be appreciated that a hoop structure which is not part of a patient interface may be formed separately and used with the patient interface.

In yet other forms not shown, the patient interface 3000 may comprise one or more sensors. The sensor(s) may be located on the inflatable body 3800, for example, or in other forms where the inflatable body 3800 is not located in use on the patient's chin region (e.g. the inflatable body 3800 is located on the top of the patient's head), the sensor(s) may be located on the chin portion, e.g. the chin strap, described herein. The sensor(s) may be configured to detect resistance to the chin strap force, i.e. the magnitude of the force on the patient's chin and/or lower jaw region in a substantially inferior direction relative to the patient's head. For example, the sensor(s) may be a force sensor, e.g. a transducer, configured to detect the force of the patient's chin acting against a chin-contacting surface of the inflatable body 3800, or the chin portion. The sensor(s) may be connected (e.g. remotely) to a processor of a RPT device as described herein. The sensor(s) may generate one or more sensor signals which the processor of the RPT device can receive and process. The processor can then trigger the RPT device to increase the pressure of the gas supplied to the inflatable body 3800 so that the chin strap force can be increased as described above, to help limit or prevent mouth leak or mandible movement. This arrangement may preferably be used where the pressure in the plenum chamber 3200 can be different to the pressure in the inflatable body 3800.

Another benefit of the present technology is that the inflatable body 3800 may be tightened or loosened to adjust the fit of the positioning and stabilising structure 3300 on the patient's head. For example, as has already been described, when the inflatable body 3800 is inflated, the positioning and stabilising structure 3300 may be tensioned or tightened. Therefore, when the inflatable body 3800 is deflated, e.g. the pressure of the gas supplied to the inflatable body 3800 is reduced or the supply of pressurised gas is stopped, the positioning and stabilising structure 3300 may be loosened. In this way the top strap 3510 and the chin strap 3530 may be tightened or loosened to tighten or loosen the fit of the positioning and stabilising structure 3300.

The benefit of this arrangement is that when the inflatable body 3800 is deflated, the patient can more easily don or doff the patient interface 3000 because the fit of the positioning and stabilising structure 3300 is loosened.

The other benefit of this arrangement is that the positioning and stabilising structure 3300 may be suitable for use by patients with different sized heads.

In some forms, the tension of the chin portion, e.g. chin strap 3530 may be lower when the patient is exposed to a lower therapy pressure compared to the tension of the chin portion, e.g. chin strap 3530, at a higher therapy pressure. For example, the RPT device 4000 may provide the lower therapy pressure while the patient falls asleep. This may provide another benefit of the present technology in that the chin portion, e.g. the chin strap 3530, may not need to be tensioned so tightly when donned so that it prevents mandible movement at the highest potential therapy pressure the patient will be exposed to. In other words, the tension of the chin strap 3530 may not need to be greater than is necessary to resist mandible movement at other times, e.g. when the therapy pressure is lower. This is in contrast to existing arrangements, as already discussed. As a result, the creation of excess strap tension, e.g. top strap 3510 and/or chin strap 3530 tension, may be limited or prevented by the present technology. This may help limit or prevent the chances of marking the patient's skin which can be caused by excess strap tension, and/or may make it easier for the patient to fall asleep.

4.3.5 Connection Port

Connection port 3600 allows for connection of the patient interface 3000 to an air circuit 4170 as described herein.

The patient interface 3000 may comprise the air circuit 4170, e.g. an air delivery conduit. The patient interface 3000 may be configured to connect to the air delivery conduit. For example, the patient interface 3000 comprises the connection port 3600.

As illustrated in the figures, and as described above, the connection port 3600 may be provided to the inflatable body 3800.

However, in other forms not shown, the connection port 3600 may be provided to the plenum chamber 3200. In these alternative forms, the inflatable body 3800 may either be connected to at least one of the plenum chamber 3200, the air delivery tube, or the RPT device, for example, via a separate conduit.

4.3.6 Vent Structure

A patient interface 3000 according to some examples of the present technology comprise a vent structure 3400 configured to allow a flow of gases exhaled by the patient from an interior of the plenum chamber 3200 to ambient. The vent structure 3400 may be configured such that the vent flow rate has a magnitude sufficient to reduce rebreathing of exhaled CO2 by the patient while maintaining the therapeutic pressure in the plenum chamber 3200 in use.

In preferred forms, the vent structure 3400 comprises a plurality of vent holes. In one form, the vent holes may be provided to the plenum chamber 3200.

4.3.7 Diffuser

A patient interface 3000 according to some examples of the present technology comprise a diffuser (not shown) to diffuse the flow of gases. The diffuser may be positioned in use to diffuse the flow of gases exiting the vent structure 3400.

4.3.8 Decoupling Structure(s)

In one form the patient interface 3000 includes at least one decoupling structure, for example, a swivel or a ball and socket.

The decoupling structure may be provided by the folds 3810 and/or thinned regions on the inflatable body 3800. This may limit or prevent forces created by the air circuit 4170, e.g. the air delivery conduit, from being transmitted to the plenum chamber 3200 and seal-forming structure 3100, which may disrupt the seal. Therefore, the inflatable body 3800 may act as a gimbal-like structure which may assist in decoupling air delivery conduit forces.

4.3.9 Forehead Support

In one form, the patient interface 3000 includes a forehead support 3700.

4.3.10 Anti-Asphyxia Valve

In one form, the patient interface 3000 includes an anti-asphyxia valve.

4.3.11 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

4.4 Other Examples of Patient Interfaces

4.4.1 Patient Interface with Lever Arrangement

Referring now to FIGS. 8 and 9, according to another aspect of the present technology, a patient interface 3000A may comprise a lever arrangement 3350.

As illustrated, the lever arrangement 3350 may be provided by a forehead support 3700, as described herein. However, in other forms which are not shown, the lever arrangement may be provided by one or more other lever members or lever arms which are positioned in use on other parts of the patient's face and/or head, e.g. the patient's chin region or the top of the patient's head.

As illustrated, the lever arrangement 3350 may be connected to the plenum chamber 3200. For instance, the lever arrangement 3350 may be attached to or integrally formed with the plenum chamber 3200.

The plenum chamber 3200 may be constructed from a material which is more rigid than the material used to construct the seal-forming structure 3100. This rigidity or stiffness may limit or prevent the plenum chamber 3200 from being compressed or collapsing when the lever arrangement 3350 is activated, as will be described in more detail below. This arrangement may help transfer forces from the lever arrangement 3350, when activated, to the seal-forming structure 3100 to help improve the seal with the patient's face.

In examples, the plenum chamber 3200 may comprise a frame 3250. The frame 3250 may be made from a substantially rigid material, e.g. a semi-rigid or rigid material, with respect to the material used to make the seal-forming structure 3100. In other forms, the plenum chamber 3200 may be stiffened or rigidised in one or more regions, e.g. by one or more rigidiser components which are attached to or formed on the plenum chamber 3200.

The patient interface 3000A may comprise an inflatable body 3800A. The inflatable body 3800A may have a similar or the same structure as the inflatable body 3800, as described above, e.g. it may be in the form of bellows with one or more folds 3810 and/or thinned regions (not shown), and may be operated in a similar manner As illustrated, the lever arrangement 3350 may comprise the inflatable body 3800A. The inflatable body 3800A is positioned in use between the underside of the lever arrangement 3350 and a region of the patient's face and/or head. For instance, the inflatable body 3800A is attached to the forehead support 3700, as illustrated. Therefore, as shown, the inflatable body 3800A may be positioned in use between the forehead support 3700 and the patient's forehead.

In a similar fashion to the inflatable body 3800, described above, when the inflatable body 3800A is inflated it creates a force which acts on a surface of the patient's head and/or face, e.g. the forehead. This in turn creates a reaction force which acts on the lever arrangement 3350, i.e. a force which is transmitted from the patient's head and/or face to the lever arrangement 3350 when the inflatable body 3800A is inflated.

The patient interface 3000A comprises a fulcrum O on which the lever arrangement 3350 pivots. As is perhaps best shown in FIG. 8, the fulcrum O is located at a connection point between a portion of the positioning and stabilising structure 3300, e.g. a strap 3500, and the lever arrangement 3350, e.g. the forehead support 3700. The forehead support 3700 may form part of the positioning and stabilising structure 3300.

At least one strap or portion, e.g. strap 3500, may extend in use around the rear of the patient's head and connect to the forehead support 3700. As illustrated, the strap 3500 is connected to the forehead support 3700 at the fulcrum O which is proximate the patient's brow.

The positioning and stabilising structure (not shown in FIG. 9) provides a headgear tension force T, the direction of which is indicated in FIG. 9.

The lever arrangement 3350 pivots on the fulcrum O when the inflatable body 3800A is inflated to create a force which acts on the plenum chamber 3200 and seal-forming structure 3100. This may increase the sealing force of the seal-forming structure 3100 on the patient's face, and in turn increases a seal reaction force CR from the patient's face to help improve the seal. These forces may be relieved when the inflatable body 3800A is deflated, which can facilitate removal of the patient interface 3000A from the patient's head and/or face.

Referring again to FIG. 9, the inflatable body 3800A has an area A1 which is the area of the inflatable body 3800A projected in a substantially anterior direction relative to the patient's face, e.g. along the x-axis which is indicated in FIG. 9. The plenum chamber 3200 and seal-forming structure 3100 (which defines a breathing chamber) has an area A2 which is the area of the breathing chamber projected in the same direction, e.g. along the x-axis. The lever arrangement 3350, e.g. forehead support 3700, has a first portion with a length L1, and a second portion with a length L2. Length L1 is the distance from the centre of the inflatable body 3800A to the fulcrum O. Length L2 is the distance from the centre of the plenum chamber 3200 to the fulcrum O.

The fulcrum O is located between the first end and the second end of the lever arrangement 3350, e.g. between the superior end 3702 and the inferior end 3704. The fulcrum O may be located between a superior end region of the inflatable body 3800A and an inferior end region the plenum chamber 3200, preferably between an inferior end of the inflatable body 3800A and a superior end of the plenum chamber 3200.

L1 and/or A1 can be increased relative L2 and/or A2, or length L2 and/or area A2 can be decreased relative to L1 and/or A1 to increase the seal reaction force or sealing force.

In other forms which are not shown, the fulcrum O may be adjusted to increase L1 and decrease L2, and vice versa. For instance, the connection point between the positioning and stabilising structure 3300, e.g. strap 3500, and the lever arrangement 3350, e.g. the forehead support 3700, may be adjusted. The forehead support 3700 may be configured to provide various connection points for the strap 3500 to attach to, e.g. it has a plurality of spaced apart headgear connectors.

In yet other forms which are not shown, the inflatable body 3800A and/or the plenum chamber 3200/seal-forming structure 3100 arrangement may be interchangeable with larger or smaller sized components. In this way, A1 and A2 may be adjusted. For instance, the forehead support 3700 may be removed from the plenum chamber 3200 and connected to a larger or smaller plenum chamber 3200, as required. The inflatable body 3800A could be adjusted in a similar fashion.

The positioning and stabilising structure 3300 provides a headgear tension force in use, e.g. the strap 3500 provides the headgear tension force. An example of a headgear tension force T and the direction of the force is indicated in FIG. 9.

The positioning and stabilising structure 3300 may comprise one or more straps or portions which are located in use such that each of the straps or portions extend across a top region of the patient's face, e.g. above the patient's cheeks, preferably above the patient's eyes or brow. In other words, the positioning and stabilising structure 3300 may not have any strap(s) or portions located in use so that they extend across regions of the patient's face that are below the patient's cheeks, eyes and/or brow. Therefore, the positioning and stabilising structure 3300 may not need to contact a lower region of the patient's face. The benefit of this is that there may be fewer components contacting parts of the patient's face, e.g. the cheeks, which may increase overall comfort during use. In addition, this arrangement may remove any straps or portions below the eyes and from the patient's line of sight.

The positioning and stabilising structure 3300 may comprise one or more straps which are provided to only the forehead support 3700. As illustrated, only a single strap 3500 may be required to hold the patient interface 3000A on the patient's face and create an effective seal. Therefore, the patient interface 3000A may not require a strap(s) which are provided to the plenum chamber 3200 that extend across the lower region of the patient's head and/or face. This can improve comfort and compliance as the positioning and stabilising structure 3300 may include fewer straps.

However, in other forms which are not shown, one or more other straps may be connected to other parts of the patient interface, e.g. another strap which connects to the plenum chamber 3200. Therefore, in other forms, the patient interface 3000A may have strap(s) or portion(s) which are located in use below the eyes and/or that extends across the patient's cheeks.

It is to be appreciated that in some forms, the patient interface 3000A may be configured to facilitate adjustment of the sealing force or the seal reaction force.

For instance, the pressure inside the inflatable body 3800A may be increased or decreased to adjust these forces. This would generally require the inflatable body 3800A to be connected to a supply of gas separately from the supply of gas entering the plenum chamber 3200, e.g. via the air circuit 4170.

The patient interface 3000A may be configured to adjust headgear tension. For instance, the patient interface 3000A may be configured to decrease headgear tension when the inflatable body 3800A is deflated, e.g. in the absence or decrease of pressure therapy in embodiments where the pressure differential between the breathable gas supplied to the patient and the gas inside the inflatable body 3800A is substantially zero. The patient interface 3000A may be configured to increase headgear tension when the inflatable body 3800A is inflated, e.g. when the pressure therapy is activated or increased in embodiments where the pressure differential between the breathable gas supplied to the patient and the gas inside the inflatable body 3800A is substantially zero.

This arrangement may allow for a lower headgear tension in the absence of therapy. The lower headgear tension may help improve donning and doffing the patient interface 3000A before and after therapy.

In the example shown in FIG. 8, the forehead support 3700 is a conduit 3710 which fluidly connects to the plenum chamber 3200. Therefore, the forehead support 3700 may comprise the connection port 3600 which connects to the air circuit 4170, e.g. air delivery conduit, as described herein. In this arrangement, the air circuit 4170 may connect to the patient interface 3000A adjacent a top region of the patient's head.

The inflatable body 3800A shown in FIG. 8 may be fluidly connected to the conduit 3710.

However, in other examples the inflatable body 3800A may be fluidly connected to at least one of the plenum chamber 3200, the air circuit 4170, and the RPT device 4000 via a separate conduit. Therefore, in examples, the inflatable body 3800A may not be fluidly connected to the conduit 3710.

In the example shown in FIG. 9, the air circuit 4170, e.g. an air delivery conduit, connects to the plenum chamber 3200, e.g. a front region of the plenum chamber 3200. Therefore, the connection port 3600 is provided to the plenum chamber 3200. The inflatable body 3800A is fluidly connected to at least one of the plenum chamber 3200, the air circuit 4170, and the RPT device 4000 via a separate conduit (not shown in FIG. 9).

In some forms, the patient interface may include a vent structure (not shown in FIGS. 8 and 9). The vent structure may have a similar or the same structure as the vent structure 3400 described herein. Therefore, the vent structure may be provided on the plenum chamber 3200.

In other forms not shown, a vent structure may be provided to the inflatable body 3800A, e.g. one or more vent holes located on the inflatable body 3800A. It may be desirable to vent air from the inflatable body 3800A to ambient. The vent structure may be configured to direct the flow of vented air onto the patient's head and/or face. For example, the direction an outlet of the vent structure faces is towards the patient's skin. This may help cool regions of the patient's face and/or head. This may improve patient comfort and therapy compliance.

For instance, a vent hole(s) located on the inflatable body 3800A may direct the flow of vented air onto the patient's forehead, for example, to keep it cool. However, it is to be appreciated that in other forms, the vent structure on the inflatable body 3800A may direct vented air away from the patient's face and/or head, as this may be more desirable in certain instances.

In other forms which are not shown, a patient contacting surface of the inflatable body 3800A, e.g. the surface which contacts in use the patient's head and/or face, may be made from at least one of a thermally conductive material, e.g. a thermally conductive metal or plastic, and a composite material with high thermal conductivity. This may facilitate in removing heat from parts of the patient's head and/or face, e.g. the forehead, which may help cool the patient. This may improve patient comfort and may lead to better therapy compliance. This arrangement may be beneficial for patients with a history of insomnia symptoms, such as sleep onset latency.

The inflatable body 3800A may act as a cushion. For example, the inflatable body 3800A cushions the forehead support 3700. This may increase comfort and may help improve therapy compliance when using a patient interface comprising a forehead support 3700.

In other forms which are not shown, the patient contacting surface may comprise a grip. The grip may be configured to provide friction between the patient's face and/or head, e.g. the forehead, and the patient contacting surface. The grip may be used to help locate and stabilise the patient interface 3000A on the patient's head and/or face during therapy, and it may limit or prevent the patient interface 3000A from moving relative to the patient's head and/or face, e.g. from sliding up or down on the patient's face.

As illustrated, the patient interface 3000A may be in the form of a nasal mask. A nasal mask may include nasal prongs, pillows or the like, a nasal cradle seal or a nasal cushion that seals around the patient's nose, as shown in the figures.

However, it is envisaged that in other forms which are not shown, the patient interface 3000A may comprise a full-face or oro-nasal mask, e.g. an under-the-nose or nasal cradle patient interface.

4.4.2 Patient Interface with Inflatable Seal-Forming Structure

Referring now to FIG. 10, according to another aspect of the present technology, a patient interface 3000B has a seal-forming structure 3100A which comprises an inflatable body 3800B, i.e. an inflatable seal-forming structure 3100A.

As illustrated, the plenum chamber 3200 may comprise a frame 3250.

The inflatable body 3800B may extend around at least a portion of a perimeter of the seal-forming structure 3100A, preferably around the entire perimeter of the seal-forming structure 3100A. As illustrated, the inflatable body 3800B may engage the patient's face in use such that it forms a seal around the patient's nose and mouth.

The plenum chamber 3200 may comprise the connection port 3600 which connects to the air circuit 4170, e.g. an air delivery conduit, as described herein.

Pressurised gas may be supplied to the inflatable body 3800B by a first conduit 4170A which is connected to the RPT device, and a second conduit (e.g. air circuit 4170) which is connected to the RPT device may supply the breathable pressurised gas to the plenum chamber 3200.

As, illustrated, the first conduit 4170A fluidly connects to a bottom region of the inflatable body 3800B. This positions the first conduit 4170A so that it is out of the patient's line of sight. Preferably, the first conduit 4170A connects to a part of the inflatable body 3800B which is positioned below the second conduit/air circuit 4170.

As illustrated, the first conduit 4170A may be attached to the second conduit/air circuit 4170. The first conduit 4170A may extend along the length of the second conduit 4170. As shown, the first conduit 4170A may extend from the underside of an superior end region of the second conduit 4170 to the part of the inflatable body 3800B to which it connects.

The cross-sectional area of the first conduit 4170A is substantially smaller than the cross-sectional area of second conduit/air circuit 4170, as shown.

The inflatable body 3800B is structured to operate in a similar manner to the inflatable body 3800, 3800A described herein, and may comprise one or more of the same features and may lead to one or more of the same advantages already discussed. However, in this particular embodiment, the inflatable body 3800B is located where the patient interface 3000B seals with the patient's face, i.e. the seal-forming structure 3100A.

Therefore, the inflatable body 3800B may be configured to limit or prevent deformation of the seal-forming structure 3100A in a first region and facilitate deformation in a second region. The second region may be configured to deform inwards into the breathing chamber A, and the first region may be configured to restrict deformation outwards and away from the breathing chamber A, as described further below.

In some forms of the present technology, the stiffness of the inflatable body 3800B may be varied in or more regions. For instance, the inflatable body 3800B may comprise a first region and a second region which has a different stiffness to the first region.

As illustrated, the inflatable body 3800A may have a first wall 3810A and a second wall 3820A. The first wall 3810A may be stiffer than the second wall 3820A. The first wall 3810A is an outer wall which faces in a direction extending outwards and away from the breathing chamber A created by the plenum chamber 3200 and the seal-forming structure 3100A, and the second wall 3820A is an inner wall which faces in a direction extending inwards and towards the breathing chamber A.

The difference in stiffness between the first wall 3810A and the second wall 3820A may be created by providing a thicker first wall 3810A compared to the thickness of the second wall 3820A, as shown. However, in other forms not shown, the variation in stiffness may be provided by one or more other means, e.g. stiffening elements such as ribs may be formed on or applied to the first wall 3810A. In addition, it is appreciated that the stiffness of the first wall 3810A may have regions with varying stiffness, e.g. thicknesses, and/or the stiffness of the second wall 3820A may have regions with differing stiffness. This may help support certain regions of the seal-forming structure 3100A more than other regions.

This arrangement may facilitate sealing with the patient's face. The second wall 3820A, which is less stiff, e g thinner, when compared to the first wall 3810A, is located on the inside of the plenum chamber 3200, and deforms towards the patient's face, resulting in a better seal being formed in that area.

In addition, the seal-forming structure 3200 may be restricted from ballooning or expanding outwards into parts of the patient's face during use, which may cause discomfort to the patient during use.

This arrangement may be used on full-face or oro-nasal masks, as shown, but also other masks or mask arrangements, including nasal masks.

Referring now to FIG. 11, in one form, the patient interface 3000B has a seal-forming structure 3100B which comprises an inflatable body 3800B, as described above, and a seal flap 3110. The seal-forming structure 3100B may include a first seal provided by the seal flap 3110 and a second seal provided by the inflatable body 3800B. Therefore, a dual-seal arrangement is provided.

As illustrated, the seal flap 3110 is located inwards of the inflatable body 3800B. In other words, the seal flap 3110 is located more proximate to the patient's airways in use than the inflatable body 3800B.

The seal-forming structure 3100B may define a chamber B between the seal flap 3110 and the inflatable body 3800B. As illustrated, the inflatable body 3800B is spaced apart from the seal flap 3110 to create the chamber B.

The seal-forming structure 3100B may comprise a flow path which extends from inside the breathing chamber A to outside or ambient. This allows for the flow of gases from inside the breathing chamber A into the chamber B, and then out of the chamber B to ambient.

The chamber B is defined by a plurality of walls. For instance, a first wall may be formed by a portion of the plenum chamber 3200, e.g. the frame 3250, a second wall may be formed by the seal flap 3110, and a third wall may formed by the second wall 3820A of the inflatable body 3800B, described above. These walls are arranged to create the chamber B.

The chamber walls may include vent structures. As illustrated, the seal flap 3110 may comprise one or more vent holes 3112. Furthermore, as shown, the first wall, e.g. the portion of the frame 3250, may comprise one or more vent holes 3114.

Therefore, the flow path or venting arrangement is created, wherein gases may flow from inside the breathing chamber through the vent hole 3112 into the chamber B, and through the chamber B to exit out through the vent hole 3114 to ambient.

During use, the air inside the breathing chamber A may be pressurised for patient therapy. The air inside the chamber B may be lower than the pressure inside the breathing chamber A due to the relative sizing of vent holes 3112 and 3114. Therefore, a pressure differential is created between the breathing chamber A and the chamber B. This may help promote sealing of the seal flap 3110 against the patient's face.

In use, the seal flap 3110 may be configured to respond to pressure inside the breathing chamber A which acts on an inner surface of the seal flap 3110 to urge it into sealing engagement with the patient's face. The lower pressure in chamber B allows part of the seal flap 3110 which is positioned against the patient's face in use to be forced towards the patient's face by the higher pressure in the breathing chamber A.

In preferred forms, the seal flap 3110 comprises a substantially thin membrane. The thickness of the seal flap 3110 may be varied along its length. For example, as shown, the part of the seal flap 3110 which is positioned against the patient's face may be thinner than an adjacent part of the seal flap 3110.

The inflatable body 3800B may be expanded in use and seals on the patient's skin when headgear forces are applied to the patient interface. Therefore, should any air leak under the seal flap 3110, then the inflatable body 3800B provides a back-up seal.

One of the benefits of this dual-seal arrangement is that the amount or magnitude of headgear forces required to hold the seal-forming structure 3100B to enable it to form an effective seal with the patient's face may be lower than the amount of headgear forces required to hold the seal-forming structure 3100A in place. In other words, the strap pressure needed to seal the seal-forming structure 3100B on the patient's face is lower than that required for seal-forming structure 3100A. This is because the inflatable body 3800A is the main and only seal for seal-forming structure 3100A.

The patient interface 3000B may be configured to adjust headgear tension in a similar way to that described in respect of patient interface 3000A.

In others forms not illustrated, the patient interface 3000B may comprise a lever arrangement 3350, e.g. a forehead support 3700, as described above. Therefore, the patient interface 3000B may have an inflatable body 3800A on the forehead support 3700, and the inflatable body 3800B. However, in one form, the patient interface 3000B may be provided with the forehead support 3700, but without the inflatable body 3800A on the forehead support 3700.

4.5 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH2O, or at least 10cmH2O, or at least 20 cmH2O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.5.1 RPT Device Mechanical & Pneumatic Components

An RPT device may comprise one or more of the following components in an integral unit. In an alternative form, one or more of the following components may be located as respective separate units.

4.5.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000 or 3800.

4.5.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000 or 3800.

4.5.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

4.5.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000 or 3800.

In one form, a signal from a transducer 4270 may be filtered, such as by low-pass, high-pass or band-pass filtering.

4.5.1.4.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

4.5.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 is received by the central controller 4230.

4.5.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

4.5.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

4.5.2 RPT Device Electrical Components 4.5.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

4.5.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

4.5.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

4.5.2.4 Clock

The RPT device 4000 may include a clock 4232 that is connected to the central controller 4230.

4.5.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

4.5.2.6 Protection Circuits

The one or more protection circuits 4250 in accordance with the present technology may comprise an electrical protection circuit, a temperature and/or pressure safety circuit.

4.5.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

4.5.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

4.5.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

4.5.2.9.1 Display Driver

A display driver 4292 receives as an input the characters, symbols, or images intended for display on the display 4294, and converts them to commands that cause the display 4294 to display those characters, symbols, or images.

4.5.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

4.5.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

4.5.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface pressure Pm, the respiratory flow rate Qr, and the leak flow rate Ql.

In various forms of the present technology, the pre-processing module 4310 comprises one or more of the following algorithms: interface pressure estimation 4312, vent flow rate estimation 4314, leak flow rate estimation 4316, and respiratory flow rate estimation 4318.

4.5.3.1.1 Interface Pressure Estimation

In one form of the present technology, an interface pressure estimation algorithm 4312 receives as inputs a signal from the pressure sensor 4272 indicative of the pressure in the pneumatic path proximal to an outlet of the pneumatic block (the device pressure Pd) and a signal from the flow rate sensor 4274 representative of the flow rate of the airflow leaving the RPT device 4000 (the device flow rate Qd). The device flow rate Qd, absent any supplementary gas 4180, may be used as the total flow rate Qt. The interface pressure algorithm 4312 estimates the pressure drop ΔP through the air circuit 4170. The dependence of the pressure drop ΔP on the total flow rate Qt may be modelled for the particular air circuit 4170 by a pressure drop characteristic ΔP(Q). The interface pressure estimation algorithm, 4312 then provides as an output an estimated pressure, Pm, in the patient interface 3000 or 3800. The pressure, Pm, in the patient interface 3000 or 3800 may be estimated as the device pressure Pd minus the air circuit pressure drop ΔP.

4.5.3.1.2 Vent Flow Rate Estimation

In one form of the present technology, a vent flow rate estimation algorithm 4314 receives as an input an estimated pressure, Pm, in the patient interface 3000 or 3800 from the interface pressure estimation algorithm 4312 and estimates a vent flow rate of air, Qv, from a vent 3400 in a patient interface 3000 or 3800. The dependence of the vent flow rate Qv on the interface pressure Pm for the particular vent 3400 in use may be modelled by a vent characteristic Qv(Pm).

4.5.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000 or 3800, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

4.5.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

4.5.3.2 Therapy Engine Module

In one form of the present technology, a therapy engine module 4320 receives as inputs one or more of a pressure, Pm, in a patient interface 3000 or 3800, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

4.5.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase Φ equal to 0 (indicating inspiration) and 0.5 (indicating expiration) respectively.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to 2π radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.

3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase Φ is first discretely estimated from the respiratory flow rate Qr as described above, as are the inhalation time Ti and the exhalation time Te. The continuous phase Φ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

4.5.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase Φ of a respiratory cycle of a patient according to a waveform template Π(Φ).

In one form of the present technology, a waveform determination algorithm 4322 provides a waveform template Π(Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template Π(Φ, t). In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

4.5.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where $0<K<1$. There is an arbitrarily large number of measures that are exactly proportional to ventilation if the flow rate shape is constant.

4.5.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow— limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

4.5.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

4.5.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

4.5.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency determination algorithm 4327 receives as an input a respiratory flow rate signal Qr, and determines the presence or absence of a cardiogenic signal. The absence of a cardiogenic signal is taken to be an indication of a closed airway.

4.5.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

4.5.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \quad (1)$$

where:

A is the amplitude, $\Pi(\Phi, t)$ is the waveform template value (in the range 0 to 1) at the current value $\Phi$ of phase and t of time, and $P_0$ is a base pressure.

If the waveform determination algorithm 4322 provides the waveform template $\Pi(\Phi, t)$ as a lookup table of values 17 indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

4.5.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 or 3800 is equal to the treatment pressure Pt.

4.5.3.4 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)

Transducer fault detection

Failure to detect the presence of a component

Operating parameters outside recommended ranges (e.g. pressure, flow rate, temperature, $PaO_2$)

Failure of a test alarm to generate a detectable alarm signal.

Upon detection of the fault condition, the corresponding algorithm 4340 signals the presence of the fault by one or more of the following:

Initiation of an audible, visual &/or kinetic (e.g. vibrating) alarm

Sending a message to an external device

Logging of the incident 4.6 Air Circuit

An air circuit 4170 in accordance with an aspect of the present technology is a conduit or a tube constructed and arranged to allow, in use, a flow of air to travel between two components such as RPT device 4000 and the patient interface 3000.

The air circuit 4170 may be referred to as an air delivery tube. As described above, the air delivery tube may be connected to the inflatable body 3800, 3800A.

The inflatable body 3800 may be positioned under the patient's chin and/or lower jaw region, as illustrated in FIGS. 6A to 6C, or in other forms not shown, the inflatable body 3800 may be positioned on top of the patient's head, for example. The benefit of this arrangement is that it creates a patient interface 3000 with a low profile, that is not bulky and obtrusive, particularly in the front of the patient's face.

However, in other forms, pressurised gas may be supplied to the inflatable body 3800, 3800B by a first conduit which is connected to the RPT device either directly or indirectly, and a second conduit which is connected to the RPT device may supply the breathable pressurised gas to the plenum chamber 3200. The first conduit can be directly connected to the RPT device or it may be connected to the second conduit to indirectly connect to the RPT device. The second conduit may be a main air delivery tube (e.g. air circuit 4170) which is connected to the RPT device, and the first conduit is a supplementary conduit which may be substantially smaller than the second conduit.

One advantage of having separate conduits is that pressure loss experienced using a single conduit to supply the pressurised gas to both the inflatable body 3800 and the plenum chamber 3200 may be limited or prevented. Therefore higher pressures may be achieved using separate conduits when compared to using a single conduit.

In particular, the air circuit 4170 may be in fluid connection with the outlet of the pneumatic block 4020 and the patient interface. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

4.7 Humidifier

4.7.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.7.2 Humidifier Components

4.7.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

4.7.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

4.7.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

4.7.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

4.7.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

4.7.2.5.1 Pressure Transducer

One or more pressure transducers 5212 may be provided to the humidifier 5000 in addition to, or instead of, a pressure sensor 4272 provided in the RPT device 4000.

4.7.2.5.2 Flow Rate Transducer

One or more flow rate transducers 5214 may be provided to the humidifier 5000 in addition to, or instead of, a flow rate sensor 4274 provided in the RPT device 4000.

4.7.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

4.7.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

4.7.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

4.7.2.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

4.8 Respiratory Therapy Modes

Various respiratory therapy modes may be implemented by the disclosed respiratory therapy system.

4.8.1 CPAP Therapy

In some implementations of respiratory pressure therapy, the central controller 4230 sets the treatment pressure Pt according to the treatment pressure equation (1) as part of the therapy parameter determination algorithm 4329. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module 4320 to determine phase $\Phi$ or the waveform template $\Pi(\Phi)$.

In CPAP therapy, the base pressure $P_0$ may be a constant value that is hard-coded or manually entered to the RPT device 4000. Alternatively, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

FIG. 4E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment $\Delta P$, provided the resulting treatment pressure Pt would not exceed a maximum treatment pressure Pmax. In one implementation, the predetermined pressure increment $\Delta P$ and maximum treatment pressure Pmax are 1 $cmH_2O$ and 25 $cmH_2O$ respectively. In other implementations, the pressure increment $\Delta P$ can be as low as 0.1 $cmH_2O$ and as high as 3 $cmH_2O$, or as low as 0.5 $cmH_2O$ and as high as 2 $cmH_2O$. In other implementations, the maximum treatment pressure Pmax can be as low as 15 $cmH_2O$ and as high as 35 $cmH_2O$, or as low as 20 $cmH_2O$ and as high as 30 $cmH_2O$. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$-Pmin, so that the decrease in $P_0$ to the minimum treatment pressure Pmin in the absence of any detected events is exponential. In one implementation, the constant of proportionality is set such that the time constant $\tau$ of the exponential decrease of $P_0$ is 60 minutes, and the minimum treatment pressure Pmin is 4 $cmH_2O$. In other implementations, the time constant $\tau$ could be as low as 1 minute and as high as 300 minutes, or as low as 5 minutes and as high as 180 minutes. In other implementations, the minimum treatment pressure Pmin can be as low as 0 $cmH_2O$ and as high as 8 $cmH_2O$, or as low as 2 $cmH_2O$ and as high as 6 $cmH_2O$. Alternatively, the decrement in $P_0$ could be predetermined, so the decrease in $P_0$ to the minimum treatment pressure Pmin in the absence of any detected events is linear.

4.8.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates $\Pi(\Phi, t)$ described above, the therapy parameter determination algorithm 4329 increases the treatment pressure Pt to $P_0$+A (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few $cmH_2O$) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 $cmH_2O$. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation (1) to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = G\int(\text{Vent} - Vtgt)dt \tag{2}$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 $cmH_2O$/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure $P_0$. As with the base pressure $P_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure $P_0$ in constant CPAP therapy.

Alternatively, the therapy parameter determination algorithm 4329 may repeatedly compute the base pressure $P_0$ during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

4.8.3 High Flow Therapy

In other forms of respiratory therapy, the pressure of the flow of air is not controlled as it is for respiratory pressure therapy. Rather, the central controller 4230 controls the pressure generator 4140 to deliver a flow of air whose device flow rate Qd is controlled to a treatment or target flow rate Qtgt that is typically positive throughout the patient's breathing cycle. Such forms are generally grouped under the heading of flow therapy. In flow therapy, the treatment flow rate Qtgt may be a constant value that is hard-coded or manually entered to the RPT device 4000. If the treatment flow rate Qtgt is sufficient to exceed the patient's peak inspiratory flow rate, the therapy is generally referred to as high flow therapy (HFT). Alternatively, the treatment flow rate may be a profile Qtgt(t) that varies over the respiratory cycle.

Glossary

For the purposes of the present technology disclosure, in certain forms of the present technology, one or more of the following definitions may apply. In other forms of the present technology, alternative definitions may apply.

4.8.4 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

4.8.4.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

4.8.4.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH2O pressure.

As an example, an I-beam may comprise a different bending stiffness (resistance to a bending load) in a first direction in comparison to a second, orthogonal direction. In another example, a structure or component may be floppy in a first direction and rigid in a second direction.

4.8.5 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

Inhalation Time (Ti): The duration of the inspiratory portion of the respiratory flow rate waveform.

Exhalation Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.8.6 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts, pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other respiratory therapy device such as an RPT device or portable oxygen concentrator, delivers a volume of breathable gas to a spontaneously breathing patient, it is said to be triggered to do so. Triggering usually takes place at or near the initiation of the respiratory portion of the breathing cycle by the patient's efforts.

4.8.7 Anatomy

4.8.7.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.8.7.2 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.8.8 Patient Interface

Anti-asphyxia valve (AAV): The component or sub-assembly of a mask system that, by opening to atmosphere in a failsafe manner, reduces the risk of excessive CO2 rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.8.9 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

4.8.9.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

4.8.9.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill)

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.8.9.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

4.8.9.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

4.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A patient interface comprising a plenum chamber pressurisable to a therapeutic pressure of at least 4 cmH2O above ambient air pressure, the plenum chamber including:

at least one plenum chamber inlet port sized and structured to receive a flow of air at the therapeutic pressure for breathing by a patient;

a seal-forming structure that is constructed and arranged to form a seal with a region of the patient's face surrounding an entrance to the patient's airways, the seal-forming structure having a hole therein such that the flow of air at said therapeutic pressure is delivered to at least an entrance to the patient's nares, wherein the seal-forming structure is constructed and arranged to maintain said therapeutic pressure in the plenum chamber throughout the patient's respiratory cycle in use, the patient interface further comprising a positioning and stabilising structure to provide a force to hold the seal-forming structure in a therapeutically effective position on the patient's head, the patient interface further comprising a hoop structure comprising:

a top portion configured to extend over a top of the patient's head;

a chin portion configured to extend below the patient's chin or lower jaw; and an inflatable body positioned, in use, between a portion of the hoop structure and the patient's head, wherein a superior region of the inflatable body is configured to, in use, contact the patient's chin and/or lower jaw region, and wherein an inferior region of the inflatable body is configured to not contact the patient in use such that the hoop structure is not configured to contact the patient below the patient's chin and/or lower jaw region.

2. The patient interface of claim 1, wherein the hoop structure is formed separately from the positioning and stabilising structure.

3. The patient interface of claim 1, wherein the hoop structure is formed as part of the positioning and stabilising structure.

4. The patient interface of claim 1, wherein the inflatable body comprises one or more folds and/or thinned regions.

5. The patient interface of claim 4, wherein the inflatable body comprises a bellows portion.

6. The patient interface of claim 1, wherein the inflatable body is positioned in use between the patient's chin and/or lower jaw region and the chin portion.

7. The patient interface of claim 1, wherein the inflatable body creates in use a force which acts on the patient's chin and/or lower jaw region, and further comprising one or more sensors configured to measure the magnitude of the force.

8. The patient interface of claim 1, wherein the top portion is connected to the chin portion by the plenum chamber and/or a frame of the patient interface.

9. The patient interface of claim 1, wherein an interior of the inflatable body is in fluid communication with an interior of the plenum chamber.

10. The patient interface of claim 1, wherein an interior of the inflatable body is not in fluid communication with an interior of the plenum chamber.

11. The patient interface of claim 1, wherein the inflatable body is detachable from the hoop structure.

12. A patient interface comprising a plenum chamber pressurisable to a therapeutic pressure of at least 4 cmH2O above ambient air pressure, the plenum chamber including:

at least one plenum chamber inlet port sized and structured to receive a flow of air at the therapeutic pressure for breathing by a patient;

a seal-forming structure that is constructed and arranged to form a seal with a region of the patient's face surrounding an entrance to the patient's airways, the seal-forming structure having a hole therein such that the flow of air at said therapeutic pressure is delivered to at least an entrance to the patient's nares, wherein the seal-forming structure is constructed and arranged to maintain said therapeutic pressure in the plenum chamber throughout the patient's respiratory cycle in use, the patient interface further comprising a positioning and stabilising structure to provide a force to hold the seal-forming structure in a therapeutically effective position on the patient's head, the patient interface further comprising a chin portion configured to extend below the patient's chin or lower jaw region, the chin portion connected to the positioning and stabilising structure, the plenum chamber, or a frame of the patient interface, and an inflatable body positioned, in use, between the chin portion and the patient's chin or lower jaw, wherein a superior region of the inflatable body is configured to, in use, contact the patient's chin and/or lower jaw region, and wherein an inferior region of the inflatable body is configured to not contact the patient in use such that the inflatable body and the chin portion are not configured to contact the patient below the patient's chin and/or lower jaw region.

13. The patient interface of claim 12, wherein the inflatable body comprises one or more folds and/or thinned regions.

14. The patient interface of claim 13, wherein the inflatable body comprises a bellows portion.

15. The patient interface of claim 12, wherein the inflatable body creates in use a force which acts on the patient's chin and/or lower jaw region, and further comprising one or more sensors configured to measure the magnitude of the force.

16. The patient interface of claim 13, wherein an interior of the inflatable body is in fluid communication with an interior of the plenum chamber.

17. The patient interface of claim 12, wherein an interior of the inflatable body is not in fluid communication with an interior of the plenum chamber.

18. A hoop structure for reducing or eliminating mouth drop in a patient during respiratory pressure therapy, the hoop structure comprising:

a top portion configured to extend over a top of the patient's head;

a chin portion configured to extend below the patient's chin or lower jaw; and an inflatable body positioned, in use, between a portion of the hoop structure and the patient's head, wherein a superior region of the inflatable body is configured to, in use, contact the patient's chin and/or lower jaw region, and wherein an inferior region of the inflatable body is configured to not contact the patient in use such that the hoop structure is not configured to contact the patient below the patient's chin and/or lower jaw region.

* * * * *